United States Patent
Volpe

(10) Patent No.: US 12,144,647 B2
(45) Date of Patent: Nov. 19, 2024

(54) PROXIMITY BASED PROCESSING SYSTEMS AND METHODS

(71) Applicant: ZOLL Medical Corporation, Chelmsford, MA (US)

(72) Inventor: Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 18/178,050

(22) Filed: Mar. 3, 2023

(65) Prior Publication Data

US 2023/0277131 A1    Sep. 7, 2023

Related U.S. Application Data

(63) Continuation of application No. 15/454,573, filed on Mar. 9, 2017, now Pat. No. 11,617,538.
(Continued)

(51) Int. Cl.
*A61B 5/00*    (2006.01)
*A61B 5/0205*    (2006.01)
(Continued)

(52) U.S. Cl.
CPC .......... *A61B 5/6805* (2013.01); *A61B 5/0205* (2013.01); *A61B 5/021* (2013.01);
(Continued)

(58) Field of Classification Search
None
See application file for complete search history.

(56) References Cited

U.S. PATENT DOCUMENTS

| 3,724,455 A | 4/1973 | Unger |
| 3,922,665 A | 11/1975 | Curry et al. |

(Continued)

FOREIGN PATENT DOCUMENTS

| DE | 2644236 C3 | 4/1981 |
| EP | 0396048 A1 | 11/1990 |

(Continued)

OTHER PUBLICATIONS

"ATS statement: Guidelines for the Six-Minute Walk Test", American Journal of Respiratory and Critical Care Medicine, vol. 166, pp. 111-117 (2002), American Thoracic Society, <URL: http://ajrccm.atsjournals.org/cgi/content/ull/166/1/111>.

(Continued)

*Primary Examiner* — Carl H Layno
*Assistant Examiner* — Manolis Pahakis
(74) *Attorney, Agent, or Firm* — Finch & Maloney PLLC

(57) ABSTRACT

An ambulatory medical device is provided. The ambulatory medical device includes at least one sensor configured to acquire data descriptive of a patient, a memory, a user interface, and at least one processor coupled with the memory, the at least one sensor, and the user interface. The at least one processor is configured to determine whether the ambulatory medical device is within a predefined range of a reference location and to initiate location-specific processing in response to determining that the ambulatory medical device is within the predefined range. The location-specific processing includes at least one of issuing a notification and adapting the user interface.

28 Claims, 12 Drawing Sheets

Related U.S. Application Data

(60) Provisional application No. 62/307,811, filed on Mar. 14, 2016.

(51) Int. Cl.

| | |
|---|---|
| *A61B 5/021* | (2006.01) |
| *A61B 5/024* | (2006.01) |
| *A61B 5/08* | (2006.01) |
| *A61B 5/11* | (2006.01) |
| *A61B 5/113* | (2006.01) |
| *A61B 5/145* | (2006.01) |
| *A61B 5/33* | (2021.01) |
| *A61B 7/00* | (2006.01) |
| *A61N 1/00* | (2006.01) |
| *A61N 1/04* | (2006.01) |
| *A61N 1/36* | (2006.01) |
| *A61N 1/372* | (2006.01) |
| *A61N 1/39* | (2006.01) |
| *H04W 4/02* | (2018.01) |

(52) U.S. Cl.
CPC ........ *A61B 5/1112* (2013.01); *A61B 5/14532* (2013.01); *A61B 5/14542* (2013.01); *A61B 5/33* (2021.01); *A61B 5/4836* (2013.01); *A61N 1/00* (2013.01); *A61N 1/0484* (2013.01); *A61N 1/36* (2013.01); *A61N 1/37247* (2013.01); *A61N 1/37282* (2013.01); *A61N 1/3904* (2017.08); *H04W 4/023* (2013.01); *A61B 5/0022* (2013.01); *A61B 5/02438* (2013.01); *A61B 5/0816* (2013.01); *A61B 5/113* (2013.01); *A61B 5/14507* (2013.01); *A61B 5/7282* (2013.01); *A61B 7/003* (2013.01)

(56) References Cited

U.S. PATENT DOCUMENTS

| | | |
|---|---|---|
| 4,094,310 A | 6/1978 | McEachern et al. |
| 4,576,170 A | 3/1986 | Bradley et al. |
| 4,580,572 A | 4/1986 | Granek et al. |
| 4,583,547 A | 4/1986 | Granek et al. |
| 4,632,122 A | 12/1986 | Johansson et al. |
| 4,729,377 A | 3/1988 | Granek et al. |
| 4,926,879 A | 5/1990 | Sevrain et al. |
| 4,928,690 A | 5/1990 | Heilman et al. |
| 4,991,217 A | 2/1991 | Garrett et al. |
| 5,078,134 A | 1/1992 | Heilman et al. |
| 5,224,479 A | 7/1993 | Sekine |
| 5,348,008 A | 9/1994 | Bornn et al. |
| 5,365,932 A | 11/1994 | Greenhut |
| 5,381,798 A | 1/1995 | Burrows |
| 5,472,453 A | 12/1995 | Alt |
| 5,544,661 A | 8/1996 | Davis et al. |
| 5,558,098 A | 9/1996 | Fain |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,792,190 A | 8/1998 | Olson et al. |
| 5,827,196 A | 10/1998 | Yeo et al. |
| 5,865,736 A | 2/1999 | Baker, Jr. et al. |
| 5,929,601 A | 7/1999 | Kaib et al. |
| 5,944,669 A | 8/1999 | Kaib |
| 6,006,132 A | 12/1999 | Tacker, Jr. et al. |
| 6,016,445 A | 1/2000 | Baura |
| 6,065,154 A | 5/2000 | Hulings et al. |
| 6,097,982 A | 8/2000 | Glegyak et al. |
| 6,097,987 A | 8/2000 | Milani |
| 6,160,964 A | 12/2000 | Imoto |
| 6,178,343 B1 | 1/2001 | Bindszus et al. |
| 6,253,099 B1 | 6/2001 | Oskin et al. |
| 6,280,461 B1 | 8/2001 | Glegyak et al. |
| 6,304,783 B1 | 10/2001 | Lyster et al. |
| 6,336,900 B1 | 1/2002 | Alleckson et al. |
| 6,374,138 B1 | 4/2002 | Owen et al. |
| 6,390,996 B1 | 5/2002 | Halperin et al. |
| 6,405,082 B1 | 6/2002 | Borgenicht |
| 6,406,426 B1 | 6/2002 | Reuss et al. |
| 6,418,346 B1 | 7/2002 | Nelson et al. |
| 6,442,433 B1 | 8/2002 | Linberg |
| 6,546,285 B1 | 4/2003 | Owen et al. |
| 6,602,191 B2 | 8/2003 | Quy |
| 6,681,003 B2 | 1/2004 | Linder et al. |
| 6,690,969 B2 | 2/2004 | Bystrom et al. |
| 6,694,191 B2 | 2/2004 | Starkweather et al. |
| 6,751,501 B1 | 6/2004 | Schuler et al. |
| 6,804,554 B2 | 10/2004 | Ujhelyi et al. |
| 6,827,695 B2 | 12/2004 | Palazzolo et al. |
| 6,878,121 B2 | 4/2005 | Krausman et al. |
| 6,889,078 B2 | 5/2005 | Struble et al. |
| 6,889,079 B2 | 5/2005 | Bocek et al. |
| 6,908,437 B2 | 6/2005 | Bardy |
| 6,947,565 B2 | 9/2005 | Halleck et al. |
| 6,990,373 B2 | 1/2006 | Jayne et al. |
| 7,088,233 B2 | 8/2006 | Menard |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,405,653 B2 * | 7/2008 | Tice .................. G08B 21/0484 600/300 |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,534,212 B2 | 5/2009 | Baker, Jr. |
| 7,712,373 B2 | 5/2010 | Nagle et al. |
| 7,728,548 B2 | 6/2010 | Daynes et al. |
| 7,831,303 B2 | 11/2010 | Rueter et al. |
| 7,860,558 B2 | 12/2010 | Feild et al. |
| 7,953,478 B2 | 5/2011 | Vaisnys et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,290,574 B2 | 10/2012 | Feild et al. |
| 8,319,632 B1 | 11/2012 | Vaisnys et al. |
| 8,331,574 B2 | 12/2012 | Powers |
| 8,364,221 B2 | 1/2013 | Mannheimer et al. |
| 8,369,944 B2 | 2/2013 | Macho et al. |
| 8,406,842 B2 | 3/2013 | Kaib et al. |
| 8,412,323 B2 | 4/2013 | Bauer |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 9,161,723 B2 | 10/2015 | Rodriguez-Llorente et al. |
| 9,283,399 B2 | 3/2016 | Donnelly et al. |
| 9,378,637 B2 | 6/2016 | Kaib et al. |
| 9,398,007 B1 | 7/2016 | Wegener et al. |
| 9,504,423 B1 | 11/2016 | Bardy et al. |
| 9,659,475 B2 | 5/2017 | Kaib et al. |
| 9,684,767 B2 | 6/2017 | Kaib et al. |
| 10,555,704 B2 | 2/2020 | Averina et al. |
| 11,504,071 B2 | 11/2022 | Terry et al. |
| 2001/0031991 A1 | 10/2001 | Russial |
| 2002/0077689 A1 | 6/2002 | Kirkland |
| 2002/0181680 A1 | 12/2002 | Linder et al. |
| 2002/0188214 A1 | 12/2002 | Misczynski et al. |
| 2003/0004547 A1 | 1/2003 | Owen et al. |
| 2003/0032988 A1 | 2/2003 | Fincke |
| 2003/0054866 A1 | 3/2003 | Byers et al. |
| 2003/0060723 A1 | 3/2003 | Joo et al. |
| 2003/0095648 A1 | 5/2003 | Kaib et al. |
| 2003/0109904 A1 | 6/2003 | Silver et al. |
| 2003/0149462 A1 | 8/2003 | White et al. |
| 2003/0158593 A1 | 8/2003 | Heilman et al. |
| 2003/0174049 A1 | 9/2003 | Beigel et al. |

(56) References Cited

U.S. PATENT DOCUMENTS

| | | |
|---|---|---|
| 2003/0195567 A1 | 10/2003 | Jayne et al. |
| 2003/0212311 A1 | 11/2003 | Nova et al. |
| 2003/0216786 A1 | 11/2003 | Russial |
| 2004/0007970 A1 | 1/2004 | Ma et al. |
| 2004/0010294 A1 | 1/2004 | Kleine |
| 2004/0049233 A1 | 3/2004 | Edwards |
| 2004/0143297 A1 | 7/2004 | Ramsey |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0049644 A1 | 3/2005 | Warren et al. |
| 2005/0131465 A1 | 6/2005 | Freeman et al. |
| 2005/0144043 A1 | 6/2005 | Holland et al. |
| 2005/0204310 A1 | 9/2005 | De Zwart et al. |
| 2005/0246199 A1 | 11/2005 | Futch |
| 2005/0283198 A1 | 12/2005 | Haubrich et al. |
| 2005/0288599 A1 | 12/2005 | Macadam et al. |
| 2006/0015148 A1 | 1/2006 | McCabe et al. |
| 2006/0036292 A1 | 2/2006 | Smith et al. |
| 2006/0085049 A1 | 4/2006 | Cory et al. |
| 2006/0095091 A1 | 5/2006 | Drew |
| 2006/0136000 A1 | 6/2006 | Bowers |
| 2006/0178706 A1 | 8/2006 | Lisogurski et al. |
| 2006/0202816 A1 | 9/2006 | Crump et al. |
| 2006/0211934 A1 | 9/2006 | Hassonjee et al. |
| 2006/0220809 A1 | 10/2006 | Stigall et al. |
| 2006/0259080 A1 | 11/2006 | Vaisnys et al. |
| 2006/0264776 A1 | 11/2006 | Stahmann et al. |
| 2006/0270952 A1 | 11/2006 | Freeman et al. |
| 2006/0293714 A1 | 12/2006 | Salo et al. |
| 2007/0016029 A1 | 1/2007 | Donaldson et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0143864 A1 | 6/2007 | Cabana et al. |
| 2007/0161913 A1 | 7/2007 | Farrell et al. |
| 2007/0162075 A1 | 7/2007 | O'Hara |
| 2007/0162390 A1 | 7/2007 | Pancholy et al. |
| 2007/0169364 A1 | 7/2007 | Townsend et al. |
| 2007/0196320 A1 | 8/2007 | Yasin |
| 2007/0197878 A1 | 8/2007 | Shklarski |
| 2007/0232946 A1 | 10/2007 | Feild et al. |
| 2007/0239214 A1 | 10/2007 | Cinbis |
| 2007/0239220 A1 | 10/2007 | Greenhut et al. |
| 2007/0265533 A1 | 11/2007 | Tran |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0030309 A1 | 2/2008 | Darrouzet |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0097793 A1 | 4/2008 | Dicks et al. |
| 2008/0103402 A1 | 5/2008 | Stickney et al. |
| 2008/0167535 A1 | 7/2008 | Stivoric et al. |
| 2008/0177193 A1 | 7/2008 | Farringdon et al. |
| 2008/0177341 A1 | 7/2008 | Bowers |
| 2008/0183090 A1 | 7/2008 | Farringdon et al. |
| 2008/0249591 A1 | 10/2008 | Gaw et al. |
| 2008/0266118 A1 | 10/2008 | Pierson et al. |
| 2008/0287749 A1 | 11/2008 | Reuter |
| 2008/0294019 A1 | 11/2008 | Tran |
| 2008/0306560 A1 | 12/2008 | Macho et al. |
| 2008/0306562 A1 | 12/2008 | Donnelly et al. |
| 2008/0312520 A1 | 12/2008 | Rowlandson et al. |
| 2008/0312522 A1 | 12/2008 | Rowlandson et al. |
| 2008/0312709 A1 | 12/2008 | Volpe et al. |
| 2009/0018428 A1 | 1/2009 | Dias et al. |
| 2009/0066366 A1 | 3/2009 | Solomon |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0118808 A1 | 5/2009 | Belacazar et al. |
| 2009/0138059 A1 | 5/2009 | Ouwerkerk |
| 2009/0146822 A1 | 6/2009 | Soliman |
| 2009/0212984 A1 | 8/2009 | Baker |
| 2009/0221887 A1 | 9/2009 | Mannheimer et al. |
| 2009/0231124 A1 | 9/2009 | Klabunde et al. |
| 2009/0232286 A1 | 9/2009 | Hurwitz |
| 2009/0234410 A1 | 9/2009 | Libbus et al. |
| 2009/0243878 A1 | 10/2009 | Ricordi et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0312650 A1 | 12/2009 | Maile et al. |
| 2009/0318779 A1 | 12/2009 | Tran |
| 2010/0010559 A1 | 1/2010 | Zhang et al. |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0063756 A1 | 3/2010 | Agrawal et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0081962 A1 | 4/2010 | Hamaguchi et al. |
| 2010/0114243 A1 | 5/2010 | Nowak et al. |
| 2010/0151918 A1* | 6/2010 | Annambhotla ....... G06F 1/3203 340/636.1 |
| 2010/0171611 A1 | 7/2010 | Gao et al. |
| 2010/0175699 A1 | 7/2010 | Varney et al. |
| 2010/0231379 A1* | 9/2010 | Hutzler ............. G08B 21/0453 340/539.12 |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2010/0305462 A1 | 12/2010 | Callas et al. |
| 2010/0312297 A1 | 12/2010 | Volpe et al. |
| 2011/0015533 A1 | 1/2011 | Cox et al. |
| 2011/0022105 A9 | 1/2011 | Owen et al. |
| 2011/0080294 A1 | 4/2011 | Tanishima et al. |
| 2011/0093840 A1 | 4/2011 | Pynenburg et al. |
| 2011/0098765 A1 | 4/2011 | Patel |
| 2011/0106736 A1 | 5/2011 | Aharonson et al. |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1* | 11/2011 | Kaib ................... A61B 5/6823 607/5 |
| 2012/0011382 A1 | 1/2012 | Volpe et al. |
| 2012/0016361 A1 | 1/2012 | White et al. |
| 2012/0053479 A1 | 3/2012 | Hopenfeld |
| 2012/0112903 A1 | 5/2012 | Kaib et al. |
| 2012/0126975 A1 | 5/2012 | Gonzales |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0242501 A1* | 9/2012 | Tran ..................... A61B 5/0024 340/870.02 |
| 2012/0259377 A1 | 10/2012 | Freeman |

(56) References Cited

U.S. PATENT DOCUMENTS

| | | | |
|---|---|---|---|
| 2012/0277642 A1 | 11/2012 | Smith et al. | |
| 2012/0283794 A1 | 11/2012 | Kaib et al. | |
| 2012/0289809 A1 | 11/2012 | Kaib et al. | |
| 2012/0293323 A1* | 11/2012 | Kaib | A61B 5/746 340/539.12 |
| 2012/0302860 A1 | 11/2012 | Volpe et al. | |
| 2013/0013014 A1 | 1/2013 | Donnelly et al. | |
| 2013/0024382 A1 | 1/2013 | Dala et al. | |
| 2013/0060149 A1 | 3/2013 | Song et al. | |
| 2013/0076523 A1* | 3/2013 | Kwan | A61B 5/1118 340/8.1 |
| 2013/0085538 A1 | 4/2013 | Volpe et al. | |
| 2013/0113496 A1 | 5/2013 | Craige, III et al. | |
| 2013/0144355 A1 | 6/2013 | Macho et al. | |
| 2013/0171599 A1 | 7/2013 | Bleich et al. | |
| 2013/0218252 A1 | 8/2013 | Kaib et al. | |
| 2013/0231711 A1 | 9/2013 | Kaib | |
| 2013/0237861 A1 | 9/2013 | Margarida et al. | |
| 2013/0324868 A1 | 12/2013 | Kaib et al. | |
| 2013/0325078 A1 | 12/2013 | Whiting et al. | |
| 2013/0325096 A1 | 12/2013 | Dupelle et al. | |
| 2013/0325396 A1 | 12/2013 | Yuen et al. | |
| 2014/0004814 A1 | 1/2014 | Elghazzawi | |
| 2014/0031884 A1 | 1/2014 | Elghazzawi | |
| 2014/0031885 A1 | 1/2014 | Elghazzawi et al. | |
| 2014/0039839 A1 | 2/2014 | Jao et al. | |
| 2014/0039841 A1 | 2/2014 | Jao et al. | |
| 2014/0073486 A1 | 3/2014 | Ahmed et al. | |
| 2014/0125619 A1 | 5/2014 | Panther et al. | |
| 2014/0163334 A1 | 6/2014 | Volpe et al. | |
| 2014/0206974 A1 | 7/2014 | Volpe et al. | |
| 2014/0249613 A1 | 9/2014 | Kaib | |
| 2014/0277243 A1 | 9/2014 | Maskara et al. | |
| 2014/0288609 A1 | 9/2014 | Freeman | |
| 2014/0288610 A1 | 9/2014 | Freeman | |
| 2014/0296656 A1* | 10/2014 | Kasama | A61B 5/1112 600/301 |
| 2014/0303680 A1 | 10/2014 | Donnelly et al. | |
| 2014/0324112 A1 | 10/2014 | Macho et al. | |
| 2014/0336514 A1 | 11/2014 | Peyman | |
| 2014/0337826 A1 | 11/2014 | Kiaie et al. | |
| 2014/0347187 A1* | 11/2014 | Freathey | G08B 21/0272 340/573.4 |
| 2015/0005588 A1 | 1/2015 | Herken et al. | |
| 2015/0018014 A1* | 1/2015 | Phan | H04W 4/029 455/456.3 |
| 2015/0035654 A1 | 2/2015 | Kaib et al. | |
| 2015/0037636 A1 | 2/2015 | Amsler et al. | |
| 2015/0039039 A1 | 2/2015 | Macho et al. | |
| 2015/0039042 A1 | 2/2015 | Amsler et al. | |
| 2015/0039053 A1 | 2/2015 | Kaib et al. | |
| 2015/0080699 A1 | 3/2015 | Kaib et al. | |
| 2015/0106020 A1 | 4/2015 | Chung et al. | |
| 2015/0134018 A1* | 5/2015 | Bonnamy | A61N 1/3993 607/5 |
| 2015/0164436 A1 | 6/2015 | Maron et al. | |
| 2015/0223731 A1 | 8/2015 | Sahin | |
| 2015/0224330 A1* | 8/2015 | Kaib | A61N 1/3904 607/7 |
| 2015/0235541 A1 | 8/2015 | Kaib et al. | |
| 2015/0265845 A1* | 9/2015 | Sullivan | A61N 1/3975 607/8 |
| 2016/0066808 A1 | 3/2016 | Hijazi | |
| 2016/0174857 A1 | 6/2016 | Eggers et al. | |
| 2016/0278652 A1* | 9/2016 | Kaib | A61N 1/0484 |
| 2016/0328529 A1* | 11/2016 | Kaib | G16H 40/40 |
| 2017/0007129 A1* | 1/2017 | Kaib | A61N 1/3904 |
| 2017/0011210 A1 | 1/2017 | Cheong et al. | |
| 2017/0172424 A1* | 6/2017 | Eggers | A61B 8/488 |
| 2017/0193787 A1* | 7/2017 | Devdas | G08B 25/005 |
| 2017/0238401 A1* | 8/2017 | Sadwick | A61N 5/0618 315/294 |
| 2017/0278370 A1 | 9/2017 | Kaib et al. | |
| 2017/0296057 A1 | 10/2017 | Freeman et al. | |
| 2018/0032691 A1 | 2/2018 | Zur et al. | |
| 2018/0310892 A1 | 11/2018 | Perschbacher et al. | |
| 2019/0325380 A1 | 10/2019 | Johnson et al. | |
| 2020/0029843 A1 | 1/2020 | Sullivan et al. | |
| 2020/0221952 A1 | 7/2020 | Kaib et al. | |
| 2021/0121082 A1* | 4/2021 | Wild | A61B 5/0022 |

FOREIGN PATENT DOCUMENTS

| | | |
|---|---|---|
| EP | 0295497 B1 | 9/1993 |
| EP | 0335356 B1 | 3/1996 |
| EP | 0707825 A2 | 4/1996 |
| EP | 0761255 A1 | 3/1997 |
| EP | 1642616 A2 | 4/2006 |
| EP | 1455640 B1 | 1/2008 |
| EP | 1720446 B1 | 7/2010 |
| EP | 2689363 A2 | 1/2014 |
| JP | 5115450 A | 5/1993 |
| JP | 1998-505515 A | 6/1998 |
| JP | 1999-149379 A | 6/1999 |
| JP | 2002-509472 A | 3/2002 |
| JP | 2002-514107 A | 5/2002 |
| JP | 2002-000059 A | 7/2002 |
| JP | 2004-318839 A | 11/2004 |
| JP | 2006-091013 A | 4/2006 |
| JP | 2006-136707 A | 6/2006 |
| JP | 2007-522859 A | 8/2007 |
| JP | 2008-302225 A | 12/2008 |
| JP | 2008-302228 A | 12/2008 |
| JP | 2009-510631 A | 3/2009 |
| JP | 2009-521865 A | 6/2009 |
| JP | 2009-528909 A | 8/2009 |
| JP | 2009-536068 A | 10/2009 |
| JP | 2012-003311 A | 1/2012 |
| JP | 6166253 B2 | 7/2017 |
| WO | 8304171 A1 | 12/1983 |
| WO | 1997022297 A1 | 6/1997 |
| WO | 1998039061 A2 | 9/1998 |
| WO | 1998043537 A1 | 10/1998 |
| WO | 1999059465 A1 | 11/1999 |
| WO | 2000002484 A1 | 1/2000 |
| WO | 2000030529 A1 | 6/2000 |
| WO | 2004054656 A1 | 7/2004 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2009122277 A2 | 10/2009 |
| WO | 2010025432 A1 | 3/2010 |
| WO | 2010077997 A2 | 7/2010 |
| WO | 2012006524 A1 | 1/2012 |
| WO | 2012100219 A1 | 7/2012 |
| WO | 2012135059 A2 | 10/2012 |
| WO | 2012149482 A2 | 11/2012 |
| WO | 2012174659 A1 | 12/2012 |
| WO | 2013040214 A1 | 3/2013 |
| WO | 2013130957 A2 | 9/2013 |
| WO | 2014018057 A1 | 1/2014 |
| WO | 2014018160 A1 | 1/2014 |
| WO | 2014097035 A1 | 6/2014 |
| WO | 2014099986 A1 | 6/2014 |

OTHER PUBLICATIONS http:/web.archive.org/web/20030427001846/http:/www.lifecor.comiimagelib/imageproduct.asp; Published by LifeCor, Inc., 2002 on a web page owned by LifeCor Inc.

Debock et al., "Captopril Treatment of Chronic Heart Failure in the Very Old", J. Gerontol, 1994, 49:M148-M152.

International Search Report for Corresponding International Application No. PCT/US2012/030433, mailed Jul. 5, 2012.

O'Keeffe et al., "Reproducability and Responsiveness of Quality of Life Assessment and Six Minute Walk Test in Elderly Heart Failure Patients", Heart, 1998, 80:377-382.

(56) References Cited

OTHER PUBLICATIONS

International Search Report and Written Opinion from Corresponding PCT Application No. PCT/US2012/030428, mailed Nov. 7, 2012.
Association for the Advancement of Medical Instrumentation, ANSI/AAMI DF80:2003, "Medical Electrical Equipment—Part 2-4: Particular Requirements for the Safety of Cardiac Defibrillators (including Automated External Defibrillators)", 2004, ISBN1-57020-210-9; abstract; p. vi; p. 50, section 107.1.2.
International Search Report and Written Opinion from PCT/US2013/028598, mailed May 9, 2013.
Zoll Medical Corporation, "LifeVest Model WCD 3000 Operator's Manual", Pittsburgh, PA (2012).
International Search Report and Written Opinion from Corresponding PCT Application No. PCT/US2015/015199, mailed on May 14, 2015.
PCT Search Report and Written Opinion for PCT Application No. PCT/US2015/066852, mailed on May 4, 2016, 16 pages.
Herlihy et al., "The Art of Multiple Processor Programming", Chapter 1, p. 1, Mar. 3, 2008.
International Search Report and Written Opinion from Corresponding International Application No. PCT/US2011/043368, dated Nov. 17, 2011.
Wikipedia, Automated External Defibrillator, May 31, 2009, Wikipedia, Section on Mechanism of Operation.
Wikipedia, "Multi-Core Processor", Dec. 11, 2009, <URL: http://web.archive.org/web/20091211134408/http://en.wikipedia.org/wiki/Multicore_processor#Hardware>.
PCT Search Report and Written Opinion for PCT Application No. PCT/US2016/023068, mailed on Jun. 3, 2016, 14 pages.
Extended European Search Report for European Application No. 13755470.5, dated Dec. 18, 2015, 6 pages.
PCT Search Report and Written Opinion for PCT Application No. PCT/US2015/039321, Oct. 15, 2015, 14 pages.

\* cited by examiner

PROXIMITY BASED PROCESSING SYSTEMS AND METHODS

CROSS-REFERENCE TO RELATED APPLICATIONS

This is a continuation of U.S. patent application Ser. No. 15/454,573 (filed 9 Mar. 2017, now U.S. Pat. No. 11,617, 538), which claims the benefit of U.S. Provisional Patent Application No. 62/307,811 (filed 14 Mar. 2016). Each of these priority applications is herein incorporated by reference in its entirety.

BACKGROUND

This disclosure relates generally to external medical devices, and more specifically, to apparatus and processes of ambulatory medical devices that provide proximity based notifications and location determination services.

There are a wide variety of electronic and mechanical medical devices for monitoring and treating patients' medical conditions. The one or more particular medical devices used to monitor and/or treat a patient depend on the underlying medical condition with which the patient is afflicted. For example, where a patient has a medical condition that affects the patient's cardiac function (e.g., a cardiac arrhythmia), medical devices such as cardiac pacemakers or defibrillators may be used to treat the patient. In some cases, these medical devices may be surgically implanted or externally connected to the patient. Such medical devices may be used alone, or in combination with drug therapies, to treat medical conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can be administered. Other cardiac arrhythmias include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

Some medical devices operate by continuously or substantially continuously monitoring the patient's heart for treatable arrhythmias via one or more sensing electrodes and, when such is detected, applying corrective electrical pulses directly to the heart through one or more therapy electrodes. Patients use these devices while ambulatory and visiting various locations, such as their home or place of work.

SUMMARY

An ambulatory medical device is capable of and designed for moving with a patient as the patient goes about his or her daily routine. The mobility enabled by an ambulatory medical device provides for a greater quality of life for a patient undergoing treatment and also presents opportunities for improved patient care. However, this same mobility creates challenges for patients and ambulatory medical device providers. Various aspects and examples described herein leverage the mobile nature of an ambulatory medical device to beneficial effect while addressing challenges created thereby.

For example, a patient wearing an ambulatory medical device may visit various locations where medical assistance is not readily available. Thus it may be important for the health of the patient that the ambulatory medical device be in proper operating condition when the patient visits these locations. The tasks required to maintain an ambulatory medical device in proper operating condition vary between devices. For example, where the ambulatory medical device includes electrodes, the tasks required to maintain the device in proper working condition may include replacing and/or adjusting the electrodes periodically and swapping or recharging a battery that powers the device. Some tasks (e.g., replacing an electrode or swapping a battery) require a replacement component be readily available, but these replacement components may be of limited availability in some locations. In some examples, the tasks required to maintain an ambulatory medical device in proper operating condition further include maintaining software components of the medical device, as may be achieved by updating the software components to keep their versions current.

Aspects and examples disclosed herein manifest an appreciation for these and other problems facing patients and medical device providers. For instance, some examples execute automated tasks that prompt the patient and/or other persons to take the actions necessary to maintain an ambulatory medical device in proper working condition, while the patient and/or other persons are in a position to do so. In other examples, the medical device automatically executes tasks that directly maintain the ambulatory medical device in proper working condition, while the device is in position to do so.

One example is directed to an ambulatory medical device. The ambulatory medical device includes at least one sensor configured to acquire data descriptive of a patient; a memory; a user interface; and at least one processor coupled with the memory, the at least one sensor, and the user interface. The at least one processor is configured to determine whether the ambulatory medical device is within a predefined range of a reference location and to initiate location-specific processing in response to determining that the ambulatory medical device is within the predefined range, the location-specific processing comprising at least one of issuing a notification and adapting the user interface.

In the ambulatory medical device, the reference location may refer to at least one of a fixed geographic location, a location of a fixed device, and a location of a mobile device. The at least one processor may be configured to determine whether the ambulatory medical device is within the predefined range using at least one of a location of a cellular tower, dead reckoning, a global positioning system, indoor positioning system, triangulation, an indoor beacon, and signal strength. The reference location may refer to a physical location including a location of a battery charger and the location-specific processing may include issuing a notification to charge a battery. The medical device may further include the battery.

The ambulatory medical device may further include at least one capacitor coupled to the battery and at least one therapy electrode coupled to the at least one capacitor. The location-specific processing may include at least one of downloading of one or more software updates, downloading device configuration information, downloading new or updated patient parameters, downloading threshold changes to underlying monitoring parameters, and downloading threshold changes to underlying treatment parameters. The location-specific processing may include calculating at least one metric based on a physiological signal.

The location-specific processing may include transmitting a notification to the patient to perform a six minute walk test. The location-specific processing may include transmitting a notification to the patient to review a patient training module.

In the ambulatory medical device, the memory may include a template schedule listing scheduled visitations to reference locations. The location-specific processing may include identifying, in the template schedule, a next scheduled visitation to a reference location equipped to complete a task and determining that the task is due prior to the next scheduled visitation, and the notification includes a request to complete the task within the predefined range. The at least one processor may be further configured to adjust the template schedule based on sampled movement observations of the patient. The task may include taking medication. The task may include servicing a serviceable component of the ambulatory medical device. The serviceable component may include a battery. In the ambulatory medical device, determining that the task is due may include determining that the battery has a remaining runtime of less than a period of time based on the next scheduled visitation. The serviceable component may include a garment. In the ambulatory medical device, determining that the task is due may include determining that the garment has not been laundered for a period of time based on the next scheduled visitation.

In the ambulatory medical device, the reference location may refer to a caregiver facility and the location-specific processing may include adapting the user interface to interact with a caregiver. In the ambulatory medical device, the at least one processor may be further configured to determine whether the ambulatory medical device is within at least one other predefined range of at least one other reference location and to initiate the location-specific processing in response to determining that the ambulatory medical device is within the at least one other predefined range. In the ambulatory medical device, the at least one processor may be further configured to determine whether the ambulatory medical device is within at least one other predefined range of at least one other reference location and to execute a conflict resolution process that favors the reference location.

The ambulatory medical device may further comprise a network interface coupled with the at least one processor. The network interface may be configured to detect an identifier of a network, the memory stores a predefined network identifier, and the at least one processor may be configured to determine that the ambulatory medical device is within the predefined range at least in part by comparing the identifier of the network to the predefined network identifier. The identifier of the network may indicate that the network is at least one of a wired local area network, a Wi-Fi network, a BLUETOOTH network, BLE beacon identifier, and a near field communication network. The memory may store an association between the predefined network identifier and an identifier of at least one of a home of the patient, an office of the patient, and a health care facility for the patient.

In the ambulatory medical device, the at least one processor may be configured to determine whether the ambulatory medical device is within the predefined range of the reference location in response to at least one of expiration of a periodic timer, expiration of an aperiodic timer, and receipt of a request to determine the distance. The ambulatory medical device may further include a network interface coupled with the at least one processor. The at least one processor may be further configured to operate the network interface in a power conservation mode when not determining whether the ambulatory medical device is within the predefined range of the reference location. The ambulatory medical device may further include a battery. The at least one processor may be further configured to limit determining whether the ambulatory medical device is within the predefined range of the reference location when the battery has a remaining runtime of less than a predetermined period of time.

Another example is directed to a method of executing location-specific processing within an ambulatory medical device. The method includes acts of determining whether the ambulatory medical device is within a predefined range of a reference location; and initiating location-specific processing in response to determining that the ambulatory medical device is within the predefined range, the location-specific processing comprising at least one of issuing a notification and adapting the user interface.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
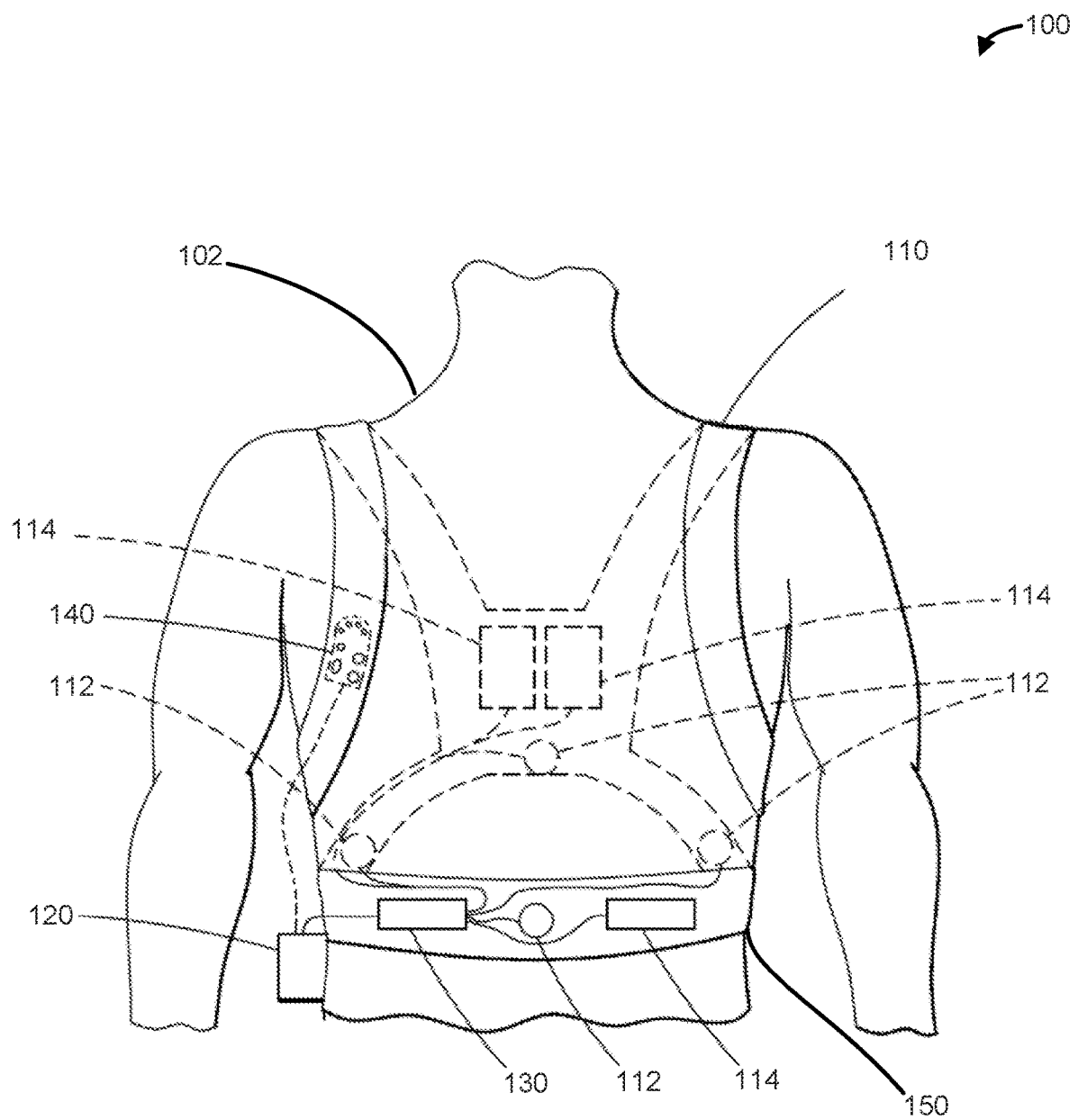
FIG. 1 is a schematic diagram of one example of a medical device in accordance with an example of the present disclosure.

Some aspects and examples are directed to apparatus and processes that monitor the location of a medical device and execute location-specific processing upon detecting that the medical device is within a predetermined range of a reference location. In various examples, this location-specific processing includes executing automated tasks that issue localized notifications to the patient or other recipients and/or adapting the user interface of the medical device to increase its relevance to the patient while the patient is within range of the reference location, and/or adapting the user interface of the medical device to increase its relevance to persons associated with the reference location. For example, the localized notifications may include reminders to maintain serviceable components of the medical device, while any materials needed to do so are readily at hand, download and/or apply software upgrades, upload certain medical device data or patient data to a base station, smartphone, or remote computer system, download and/or apply device configuration parameters, treatment data, monitoring and/or treatment thresholds and parameters, and new or updated instructions to the patient.

In some examples, the location-specific processing includes execution of one or more tasks, other than notification tasks, based on the location of the device. For example, these other tasks may include downloading and/or applying software upgrades, uploading medical device and/or patient data to a base station, mobile device, smartphone, or a remote computer system, changing device configuration parameters, updating or downloading new treatment data, changing or adding new monitoring and/or treatment thresholds and parameters, or instructions to the patient. In some cases, the information to be downloaded to and applied on the medical device may be available on a base station or another device, such as a mobile phone, within a reference location. As such, on detecting proximity to such base station or other device, the medical device can perform preconfigured tasks in response to the detected proximity.

Further, one or more adaptations of the user interface as described above may include removing some elements of the user interface, changing existing elements, and exposing new elements to, for example, the patient or professional medical personnel when the medical device is in a location associated with the personnel.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, components, elements or acts of the systems and methods herein referred to in the singular may also embrace examples including a plurality, and any references in plural to any example, component, element or act herein may also embrace examples including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

Example Medical Devices

A medical device as described herein is configured to monitor a patient and, in some implementations, provides treatment to the patient based on the monitoring. For instance, in some examples, the medical device monitors one or more physiological parameters of the patient. More particularly, the medical device can be configured to monitor data digitized from one or more physiological signals acquired from a patient (e.g., electrocardiograph (ECG) data), heart beats, respiration, breath sounds, tissue fluids, lung fluids, lung sounds, chest movements, and/or cardiopulmonary anomalies, detect anomalies present in the digitized data, and determine whether the detected anomalies impair cardiac or pulmonary function. In various implementations, the medical device can be configured to monitor other patient parameters including but not limited to blood pressure, glucose levels, weight, blood oxygen, etc.

External medical devices as described herein may be in contrasted with internal devices, such as implantable medical devices. For example, the external medical devices as described herein may be capable of continuous, substantially continuous, long-term and/or extended monitoring and/or treatment of a patient or wear by, or attachment or connection to the patient for a period of time. For instance, external medical devices as described herein may be capable of being used or worn by, or attached or connected to a patient, without substantial interruption for a predetermined period of time. In some examples, such external medical devices may be capable of being used or worn by, or attached or connected to a patient for example, up to hours or beyond (e.g., weeks, months, or even years). In some examples, the period of time may be at least 24 hours. In some examples, the period of time may be at least one week. In some examples, the period of time may be at least two weeks. In some examples, the period of time may be at least one month. A medical professional may determine an appropriate period of time based on a number of factors including the patient's underlying condition, the data being monitored, and availability of alternative therapy and/or monitoring methods among others.

Some medical devices as disclosed herein can be used as cardiac monitors in certain cardiac monitoring applications, such as holter monitoring, mobile cardiac telemetry (MCT) and/or continuous event monitoring (CEM) applications. In some instances, the medical devices may carry out monitoring in periodic or aperiodic time intervals or times. For example, the monitoring during intervals or times can be triggered by a user action or another event. The one or more durations between the periodic or aperiodic intervals or times can be user-configurable.

Example Wearable Medical Device

In some implementations, an external ambulatory medical device can be configured as a wearable defibrillator, such as the LifeVest® wearable defibrillator available from ZOLL® Medical Corporation of Chelmsford, MA FIG. 1 illustrates an example medical device 100 that is external, ambulatory, and wearable by the patient 102. As shown, the medical device 100 includes a garment 110, a plurality of sensing electrodes 112, a plurality of therapy electrodes 114, a medical device controller 120, a connection pod 130, a patient interface pod 140, and a belt 150. The plurality of sensing electrodes 112 can be disposed at various positions about the patient's body. As shown, the sensing electrodes 112 are electrically coupled to the medical device controller 120 through the connection pod 130. In some implementations, some of the components of the wearable medical device 100 are affixed to the garment 110 that can be worn on the patient's torso. For example, as shown in FIG. 1, the controller 120, at least some of the sensing electrodes 112, and, optionally, one or more therapy electrodes 114 can be mounted on a belt 150 worn by the patient. The sensing electrodes 112 and the connection pod 130 can be assembled or integrated into the garment 110 as shown. The sensing electrodes 112 are configured to monitor the cardiac function of the patient (e.g., by monitoring one or more cardiac signals of the patient). The plurality of therapy electrodes 114 can be electrically coupled to the controller 120 through the connection pod 130. The therapy electrodes 114 are configured to deliver one or more therapeutic defibrillating shocks to the body of the patient if the medical device 100 determines that such treatment is warranted. The connection pod 130 may include electronic circuitry and one or more sensors (e.g., a motion sensor, an accelerometer, etc.) that are configured to monitor patient activity.

The wearable medical device 100 may include the optional patient interface pod 140 that is coupled to the patient interface of the medical device controller 120. For example, the patient interface pod 140 may include patient interface elements such as a speaker, a microphone responsive to patient input, a display, an interactive touch screen responsive to patient input, and/or physical buttons for input. In certain implementations, the patient interface pod 140 may include some or all of the location aware components described herein (see, e.g., FIG. 4). In some of these implementations, these location aware components may utilize information descriptive of the location of the medical device 100. This location information may be derived from components included in the patient interface pod 140, such as global positioning system (GPS) devices, inertial measurement units (e.g., accelerometers, gyroscopes, etc.), and other data acquisition devices.

In some implementations, in addition to or instead of display 220, the patient may interact with the medical device 100 (e.g., receive patient input or provide information to the patient as described herein) via the patient interface pod 140. In an example, the controller 120 may be configured to detect that if the patient interface pod 140 is operatively coupled to the controller 120, the controller 120 may then disable the patient interface elements of the controller 120 (e.g., display 220) and instead communicate via the patient interface pod 140. In certain examples, the patient interface pod 140 and the user elements of controller 120 may serve as redundant input via which the patient may interact with the device 120. The patient interface pod 140 may be wirelessly coupled with the controller 120. The patient interface pod 140 may take other forms and include additional functionality. For instance, the patient interface pod 140 may be implemented on a smartphone, tablet, or other mobile device carried by the patient. In another example, the patient interface pod 140 may be worn as a watch about the wrist of the patient, or as a band about an upper arm of the patient. In some implementations, the controller 120 may communicate certain alerts and information and/or be responsive to patient input via both the patient interface elements included in the controller 120 and the patient interface pod 140. The patient and/or caregiver can interact with the touch display 220 or the patient interface pod 140 to control the medical device 100.

Example Medical Device Controller

Figure 2B:
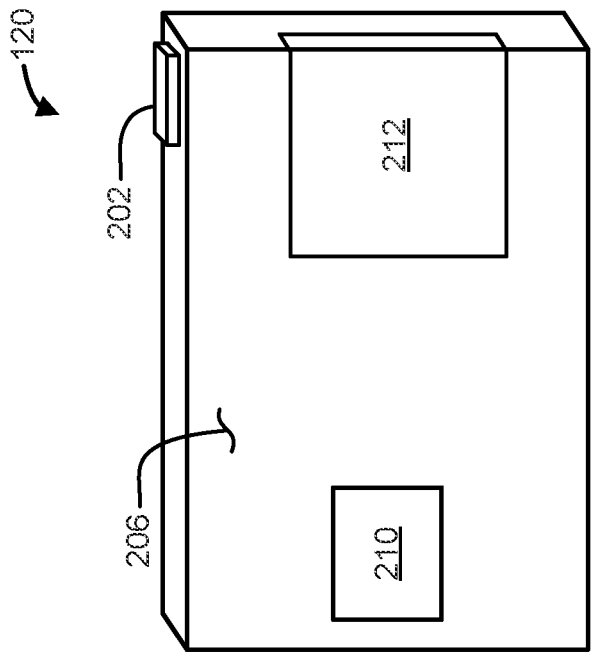
FIGS. 2A and 2B are schematic diagrams of a first side and a second side of one example of a medical device controller in accordance with an example of the present disclosure.
Figure 2A:
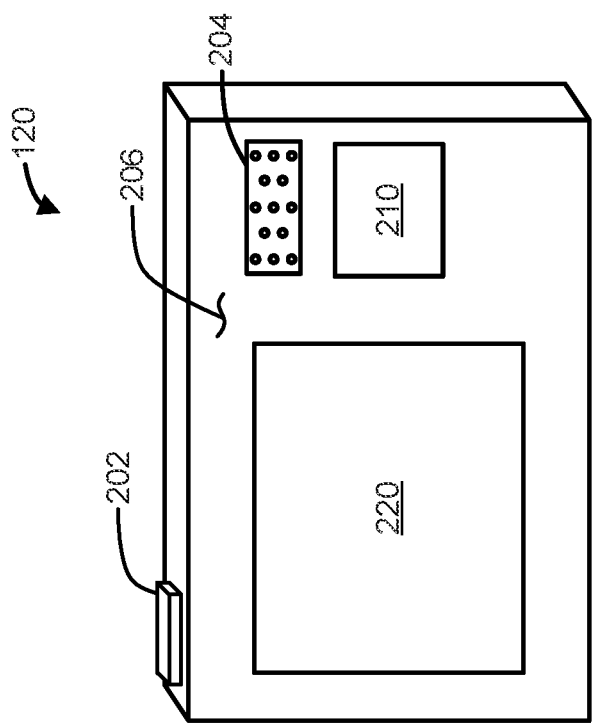

FIGS. 2A and 2B illustrate an example of the controller 120. The controller 120 includes a port 202, a speaker 204, response buttons 210, a battery 212, a display 220, and a housing 206 in which one or more location aware components are disposed. These location aware components are configured to execute location-specific processing and are described further below with reference to FIG. 4. The display 220 can be implemented as a touch screen interactive user interface. Accordingly, the patient and/or a caregiver can interact with the display 220 to control the medical device 100. In some examples, the controller 120 is configured to communicate audio information to the patient, the caregiver, and/or a bystander via the speaker 124 including audible alarms to alert the patient and bystanders to the patient's medical condition. The controller 120 can include the response buttons 210 for the patient to press to indicate that the patient is conscious, thereby instructing the controller 120 to withhold the delivery of therapeutic defibrillating shocks. If the patient does not respond to an instruction, the medical device 100 may determine that the patient is unconscious and proceed with a treatment sequence, culminating in the delivery of one or more defibrillating shocks to the body of the patient. The port 202 is configured to removably connect sensing devices (e.g., sensing electrodes 112) and/or therapeutic devices (e.g., therapy electrodes 114) to the controller 120. In some examples, the sensing electrodes 112 include ECG sensing electrodes. The controller 120 may be powered by the rechargeable battery 212.

Figure 3:
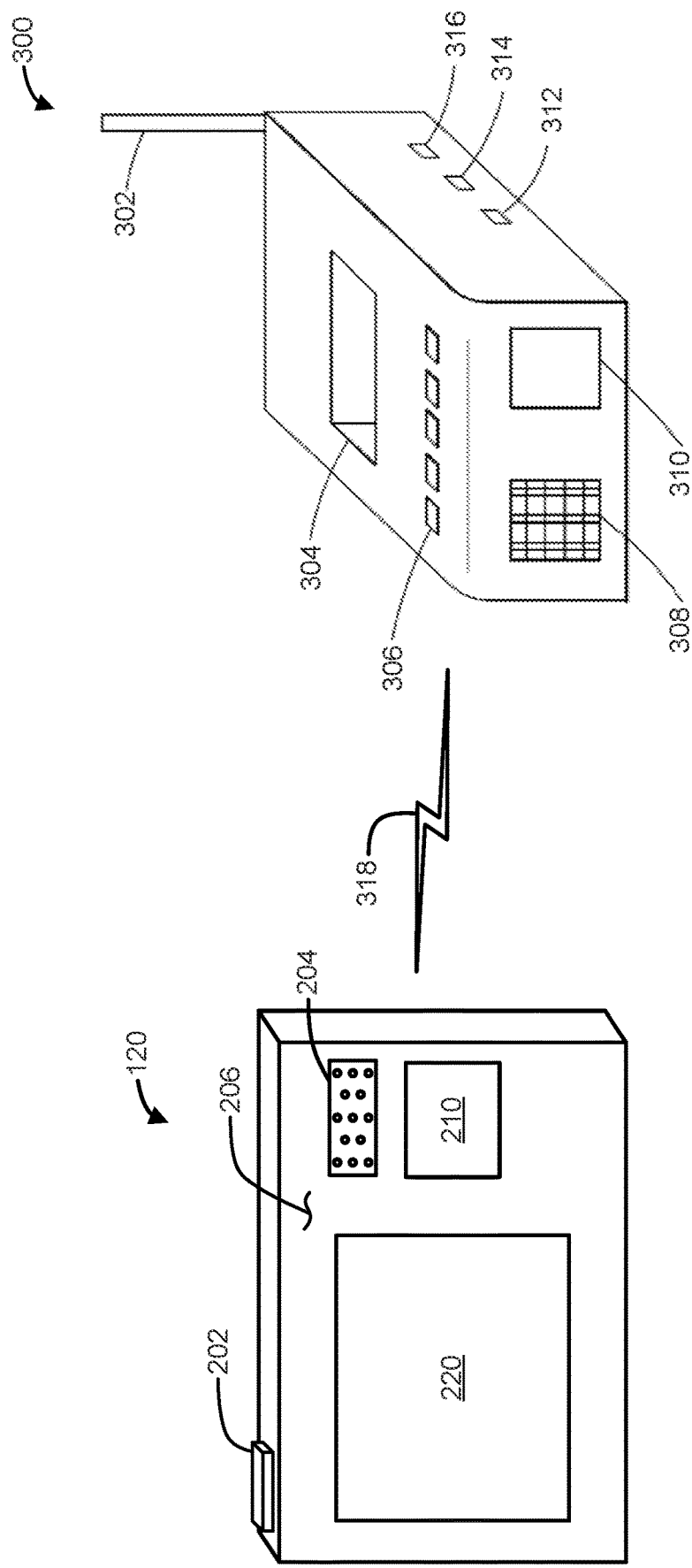
FIG. 3 is a schematic diagram of an example system including a medical device controller and a base station in accordance with an example of the present disclosure.

In some examples, the controller 120 may be in communication with a base station 300 as shown in FIG. 3. The base station 300 includes an antenna 302, a battery charging bay 304, one or more buttons 306, a speaker 308, a display 310, and one or more communication interfaces 312, 314, and 316. The base station 300 communicates with the controller 120 via, for example, a wireless communication connection 318 (e.g., BLUETOOTH, Wireless USB, ZigBee, and Wireless Ethernet). The information received by the base station 300 may be communicated over a wired or wireless communication network shortly after it is received by the base station 300, or alternatively, may be stored in a memory of the base station 300 and communicated over the network at a later time. For example, information relating to the patient's medical condition and/or device status information over a period of time may be communicated by the base station 300 to a remote server through which a caregiver, such as a physician, may remotely monitor the patient's medical condition.

Figure 4:
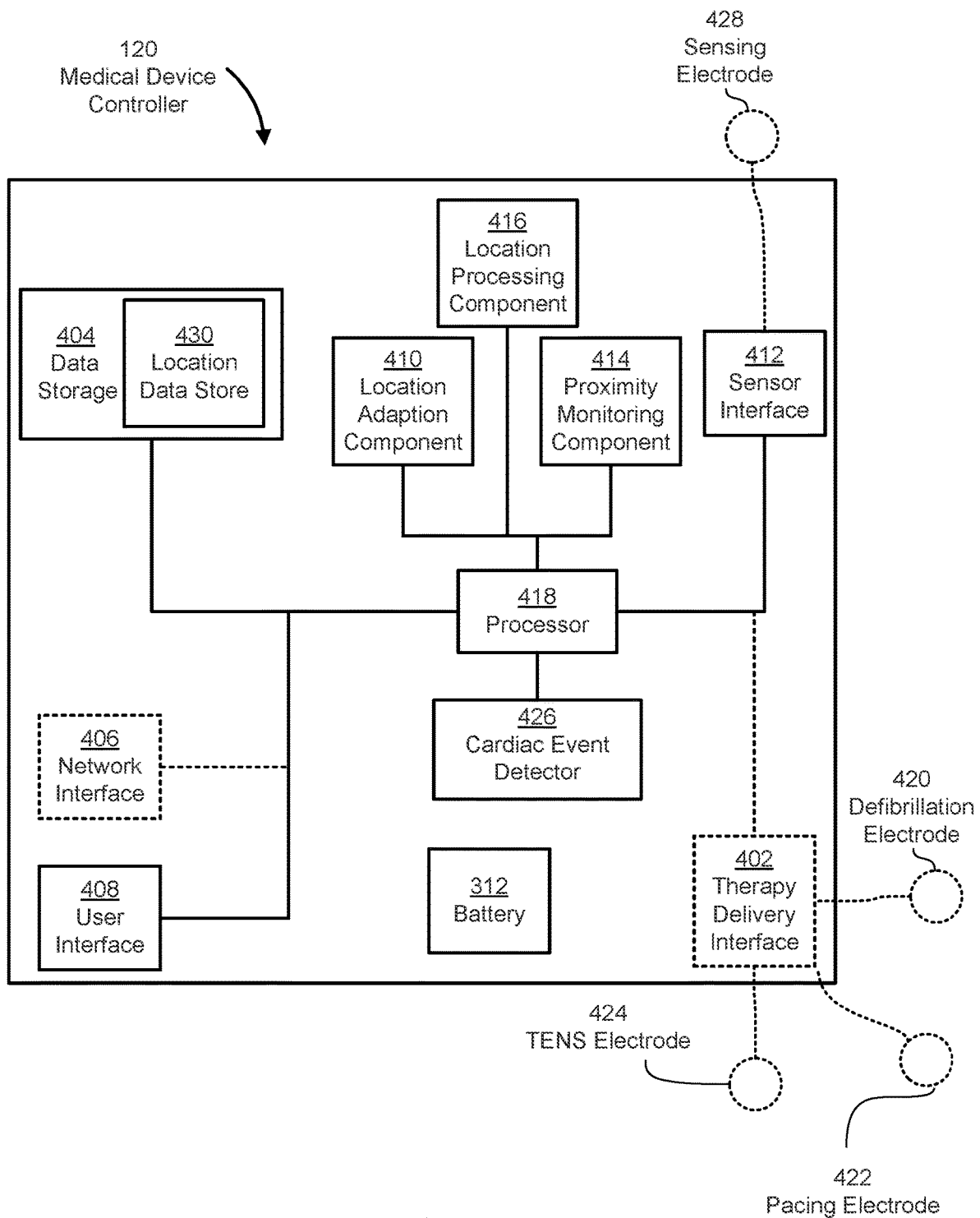
FIG. 4 is a block diagram of an example of a medical device controller in accordance with an example of the present disclosure.

FIG. 4 shows a schematic of an example of the controller 120 of FIGS. 1, 2A, 2B and 3. The controller 120 includes at least one processor 418, location adaptation component 410, a proximity monitoring component 414, a location-specific processing component 416, a sensor interface 412, an optional therapy delivery interface 402, data storage 404 (which may include location data store 430), an optional network interface 406, a user interface 408, and the battery 212. The sensor interface 412 may be coupled to any one or combination of sensors to receive information indicative of patient parameters. For example, the sensor interface 412 may be coupled to one or more sensing devices including, for example, sensing electrodes 428. The therapy delivery interface 402 (if included) may be coupled to one or more electrodes that provide therapy to the patient including, for example, one or more defibrillation electrodes 420, pacing electrodes 422, and/or TENS electrodes 424. In some examples, the sensing electrodes 428 are included in the sensing electrode 112 and the defibrillation electrode 420, the pacing electrode 422, and/or the TENS electrode 424 are included in the therapy electrodes 114. The sensor interface 412 and the therapy delivery interface 402 may implement a variety of coupling and communication techniques for facilitating the exchange of data between the sensors and/or therapy delivery devices and the controller 120. In some examples, the network interface 406 is configured to operate in a power conservation mode.

In some examples, the network interface 406 can facilitate the communication of information between the controller 120 and one or more other devices or entities over a communications network. For example, the network interface 406 may be configured to communicate with a server (e.g., a remote server) where a caregiver can access information related to the patient or with a base station (e.g., the base station 300) that is associated (e.g., paired) with the controller 120.

In some examples, the controller 120 includes a cardiac event detector 426 to monitor the cardiac activity of the patient and identify cardiac events experienced by the patient based on received cardiac signals.

In some examples, the user interface 408 includes one or more physical interface devices such as input devices, output devices, and combination input/output devices and a software stack configured to drive operation of the devices. These user interface elements may render visual, audio, and/or tactile content, including content relating to location-specific processing. For instance, in some examples, the user interface 408 includes a microphone, the speaker 204, the display 220, and the response buttons 210. Thus the user interface 408 may receive input or provide output, thereby enabling a user to interact with the controller 120.

In some implementations, the processor 418 includes one or more processors that each can perform a series of instructions that result in manipulated data and/or control the operation of the other components of the controller 120. In some implementations, when executing a specific software process as provided herein (e.g., FIGS. 5-8), the processor 418 is configured to make specific logic-based determinations based on input data received, and further capable of providing one or more outputs that can be used to control or otherwise inform subsequent processing to be carried out by the processor 418 and/or other processors or circuitry with which processor 418 is communicatively coupled. Thus, the processor 418 reacts to specific input stimulus in a specific way and generates a corresponding output based on that input stimulus. In this sense, the structure of processor 418 according to one example is defined by the flow charts shown in FIGS. 5-8. In some example cases, the processor 418 proceeds through a sequence of logical transitions in which various internal register states and/or other bit cell states internal or external to the processor 418 may be set to logic high or logic low. This specific sequence of logic transitions is determined by the state of electrical input signals to the processor 418 and a special-purpose structure is effectively assumed by the processor 418 when executing each software instruction of the software process shown in FIGS. 5-8. Specifically, those instructions anticipate the various stimuli to be received and change the implicated memory states accordingly. In this way, the processor 418 may generate and store or otherwise provide useful output signals. It is appreciated that the processor 418, during execution of a software process is capable of processing specific input signals and rendering specific output signals based on the one or more logic operations performed during execution of each software instruction. As referred to herein, the processor 418 is configured to execute a function where software is stored in a data store coupled to the processor 418 that is configured to cause the processor 418 to proceed through a sequence of various logic decisions that result in the function being executed.

In various implementations, the controller 120 implements an embedded operating system that supplies file system and networking support. In one example, the controller 120 includes software features that provide relational database functionality, touch screen display drivers, audio generation, BLUETOOTH wireless networking, BLUETOOTH Low Energy (BLE) Beacon technology, networking security and firewalling, a lightweight web server and data encryption services.

Example Location Aware Components

The proximity monitoring component 414 illustrated in FIG. 4 is configured to monitor for and detect occurrences of the controller 120 being within one or more predefined ranges of one or more reference locations. When executing according to any of various configurations, the proximity monitoring component 414 detects such occurrences by executing any of a variety of proximity detection processes. These processes may, for example, detect proximity with reference to a coordinate system (e.g., a geographic coordinate system) and/or detect proximity with reference to one or more range identifiers (e.g., identifiers that indicate the controller 120 is within one or more predefined ranges of a reference location). For example, the reference location may be based on one or more predetermined geographic coordinates (e.g., GPS coordinates of a certain physical location) or a location of a base station device (e.g., base station 300). In implementations involving base station locations, typically base stations may be associated with a physical location (e.g., a patient's home, place of work, or other location). In yet some examples, the reference location may be based on a mobile device such as a patient, caregiver or other predetermined person's smartphone or tablet. As such, one or more proximity detection processes may include detecting proximity to one or more such devices.

For instance, when executing according to its configuration in some examples, the proximity monitoring component 414 detects proximity by determining a geographic location of the controller 120, calculating a distance from the geographic location to a reference location, and comparing the distance to one or more ranges defining various proximities. The proximity monitoring component 414 may utilize a variety of technologies and techniques to determine the geographic location of the controller 120. Examples of these technologies and techniques include GPS devices, dead reckoning processes, signal strength calculations, cellular network services, WiFi network services, BLUETOOTH network services, BLE beacon technologies, radio frequency identification (RFID) devices, indoor beacons, triangulation techniques, and indoor positioning systems. In some examples, the proximity monitoring component 414 is configured to limit execution of proximity monitoring processes when the battery 212 has a remaining runtime that is less than a configurable threshold value. For example, such a threshold may be set by default to 20% of remaining battery charge capacity. Additionally, in some examples, the proximity monitoring component 414 may switch the network interface 406 into its power conservation mode when the proximity monitoring component is not actively executing a proximity monitoring process. Particular example applications of these technologies and techniques are described further below with reference to FIGS. 5, 6, 11, and 12.

In some examples, the proximity monitoring component 414 is configured to detect proximity by detecting one or more range identifiers without reference to a coordinate system. These range identifiers may include identifiers of networks available to the controller 120, identifiers of other devices available to the controller 120 via a network, identifiers of other devices detectable by the proximity monitoring component 414 (e.g., RFID tags), signal strength information, express range identifiers (e.g., as defined by the IBEACON standard as published by APPLE Inc. BLE beacon technologies, among others), visual fiduciaries, audio signals, motion patterns (e.g., as generated by a commute via car, bus or train, or ocean waves on a boat), etc. Thus, when executing according to its configuration, the proximity monitoring component 414 may interoperate with other components of the controller 120 to detect range identifiers. Examples of these other components include the network interface 406 (e.g., to detect network and device identifiers), the user interface 406 (e.g., to detect visual or audio identifiers), and the sensor interface 412 (e.g., to detect speed or motion identifiers). Particular examples of processes that the proximity monitoring component 414 is configured to execute to detect range identifiers are described further below with reference to FIGS. 5, 7, 11, and 12.

The location adaptation component 410 illustrated in FIG. 4 is configured to, in some examples, adapt operation of a medical device including the controller 120 in response to the controller being within a predefined range of a reference location. When executing according to its configuration, the location adaptation component 410 adapts the operation of the medical device by altering the information and/or options displayed via the user interface 408. For instance, the location adaptation component 410 may omit, add, and/or move user interface elements (e.g., menu selections, text boxes, graphs, etc.) in various screens presented via the user interface 408 based on the range of the controller 120 from one or more reference locations. Particular examples of processes that the location adaptation component 410 is configured to execute to adapt operations of a medical device are described further below with reference to FIGS. 5, 10, 11, and 12. One example screen adapted by the location adaptation component 410 is described further below with reference to FIG. 10.

The location-specific processing component 416 illustrated in FIG. 4 is configured to execute location-specific tasks such as issuing specialized, location-oriented notifications in response to the controller being within a predefined range of a reference location. The location-specific processing component 416 may be configured to issue these notifications to a patient, a caregiver near the patient, such as a family member, a designated person, or a loved one, and/or another such caregiver located at a remote location. For example, proximity-based notifications may be issued to both the patient and another designated person other than the patient. In some implementations, such notifications may be issued to the patient and a designated person other than the patient at substantially the same time. In some cases, the notifications may be issued with a preconfigured, programmable time delay, such that first the patient is notified, and if the patient does not respond to the notification (e.g., by acknowledging the notification), a designated person other than the patient is notified after expiration of the time delay. Communication channels for these notifications may include the user interface 408, the patient interface pod 140, a user interface of another medical device, a user interface of a programmable device (e.g., a smart phone, tablet computer, personal computer, etc.), and the like.

The content of the notifications may vary broadly between examples. For instance, in some examples, the content includes a prompt for the patient to download and apply one or more of the software patches, updates, device configuration information, new or updated patient parameters, and/or threshold changes to underlying monitoring or treatment parameters. Alternatively or additionally, the content may include a notification to the patient of a device task to be performed automatically. The content of the notifications may include a reminder for a patient to service a component of a medical device (while the patient is at a location where such servicing is available), a reminder for a patient to take medication, a reminder for a patient to review training materials, a request for a patient to perform a diagnostic or remedial physical activity, etc. In some examples, the content may include a reminder to the patient the charge a rechargeable battery when the device detects proximity to a base station equipped with a battery charger. For example, if the battery charge level is below a threshold and the patient is proximate a base station with a battery charger, the device may alert the patient that the battery needs to be charged.

As noted below, the device may adaptively learn about the patient's movements with respect to proximity to the base station over time. In adaptively providing notifications based on proximity, the device may also take into account the time of the day, the priority of the notification, the device status and, patient condition in determining when and whether to provide proximity-based notifications. As such, the device may adapt its notifications to make them more relevant to the patient in accordance with the patient's current activity. For example, if the patient is sleeping, or taking a nap, the device may suppress some or all such notifications until the patient is awake and still proximate to the base station.

In some examples, the location-specific processing component 416 is configured to execute other location-specific tasks automatically in response to detecting that the medical device controller 120 is within a predefined proximity of one or more reference locations. For instance, the location-specific processing component 416 may be configured to, when within range of a reference location, automatically calculate certain trends, metrics, and/or statistics based on the sensed physiological and/or device data, perform a data fetch operation to download one or more software updates (e.g., upgrades or patches), device configuration information, new or updated patient parameters, and/or download and apply threshold and/or other changes to underlying monitoring or treatment parameters.

For instance, within a cardiac monitor or an ambulatory external defibrillator (e.g., a wearable defibrillator), the location-specific processing component 416 can be configured to perform calculations of arrhythmia burdens and immediately transmit such information to a remote server. When executing according to this configuration, the location-specific processing component 416 monitors the signal quality and if the signal quality deteriorates or a disconnection of an electrode occurs, the location-specific processing component 416 instead records an onset and an exit event corresponding to the portion of the recording of interest and transmits the information at a later time. Other types of trends, metrics, and/or statistics may be calculated and transmitted to a remote server. For example, the location-specific processing component 416 may calculate a patient's heart rate during a predetermined period and supplement such heart rate information with additional information regarding a range of the patient's heart rate during the period, the maximum rate detected, the lowest rate detected, and an average rate. The location-specific processing component 416 may be configured to calculate atrial fibrillation (AF) metrics, including total AF burden, a number of AF episodes, and a range of the AF, including maximum, minimum, and average information. The location-specific processing component 416 may be configured to calculate a sinus rhythm metrics, including a range for sinus rhythm rate, including maximum, minimum, and average information, bradycardia burden and/or duration, bradycardia episode count, and extreme values corresponding to bradycardia episodes (e.g., longest and slowest episodes). The location-specific processing component 416 may be configured to calculate metrics relating to pauses and/or blocks, including a corresponding total burden and/or duration, missed beats (e.g., a count of such missed beats), asystole, etc. The location-specific processing component 416 may be configured to calculate supraventricular tachycardia metrics, including total burden and/or duration, premature atrial contraction (PAC) counts.

In one example, a physiological patient monitor (e.g., a cardiac monitor) or an external ambulatory treatment device (e.g., a wearable defibrillator or pacing device) including the location-specific processing component 416 may exchange information relating to cardiac monitoring and/or treatment thresholds with a remote server based on proximity to a reference location. In general, such information can include patient information, device status information, and other operational data. A cardiac monitor or a defibrillator including the location-specific processing component 416 may exchange patient information such as ECG information, such as atrial fibrillation (AF) threshold values, changes in QRS (e.g.: width, height, or other such parameter), change in (s-t) t-wave, ventricular tachycardia (VT) thresholds, ventricular fibrillation (VF) thresholds, tachycardia (e.g., above a specified threshold), bradycardia (e.g., heart rate falling below a specified threshold, significant pauses (e.g., triggered by a predetermined threshold), and pre-ventricular contractions (PVCs), e.g., when a count threshold is exceeded. Patient information may include patient reported symptom information, e.g., when the patient reports (e.g., by activation of a user interface element) dizziness, palpitations, chest pain, etc. Other patient information may include change in patient fluid levels (e.g., based on an radio-frequency wave sensor), respiration information, accelerometer-detected patient falls, walk test activation, thresholds, parameters and associated data, cardiac sounds or measures such as an S3, S4, or prolonged electromechanical activation times (EMAT). The data may be configured to be exchanged on a continuous, periodic, or aperiodic basis.

In some examples, a defibrillator including the location-specific processing component 416 may exchange information relating to treatment thresholds, such as shock energy levels, number of pulses, duration of pulses, etc. with a remote server. For example, the server receiving such information may be configured to perform analysis on the returned data, including study data trends, and provide one or more reporting functions to predetermined end-users and/or devices. For example, reports can be generated in specified intervals (e.g., weekly, daily, or hourly). Reports may also be generated based on onset of certain events (e.g., cardiac events described above).

In some examples, the location-specific processing component 416 may execute tasks that configure components of the medical device controller 120. For example, when a medical device including the location-specific processing component 416 comes within range of a predetermined reference location, the location-specific processing component 416 may download an updated configuration file. This download may involve an HTTP GET operation to get settings and action files from a specified location on the remote server (e.g., /settings/downloads/configuration/). In some examples, one or more redirection rules can be implemented at the remote server to properly direct the query to an appropriate location within the server.

The updated configuration file may include configuration information such as, a unique device record identifier, a patient identifier, configuration file path name, initial device settings and configurations, and monitoring and/or treatment threshold values. In cardiac monitoring devices, the configuration file can include event reporting settings, such as, creation of event report files, frequency of event recording and reporting, thresholds for triggering certain recordings, and recording of one or more specified parameters.

Additional examples of processes that the location-specific processing component 416 is configured to execute are described further below with reference to FIGS. 5, 8, 9, 11, and 12.

Example Location Aware Processes

Figure 5:
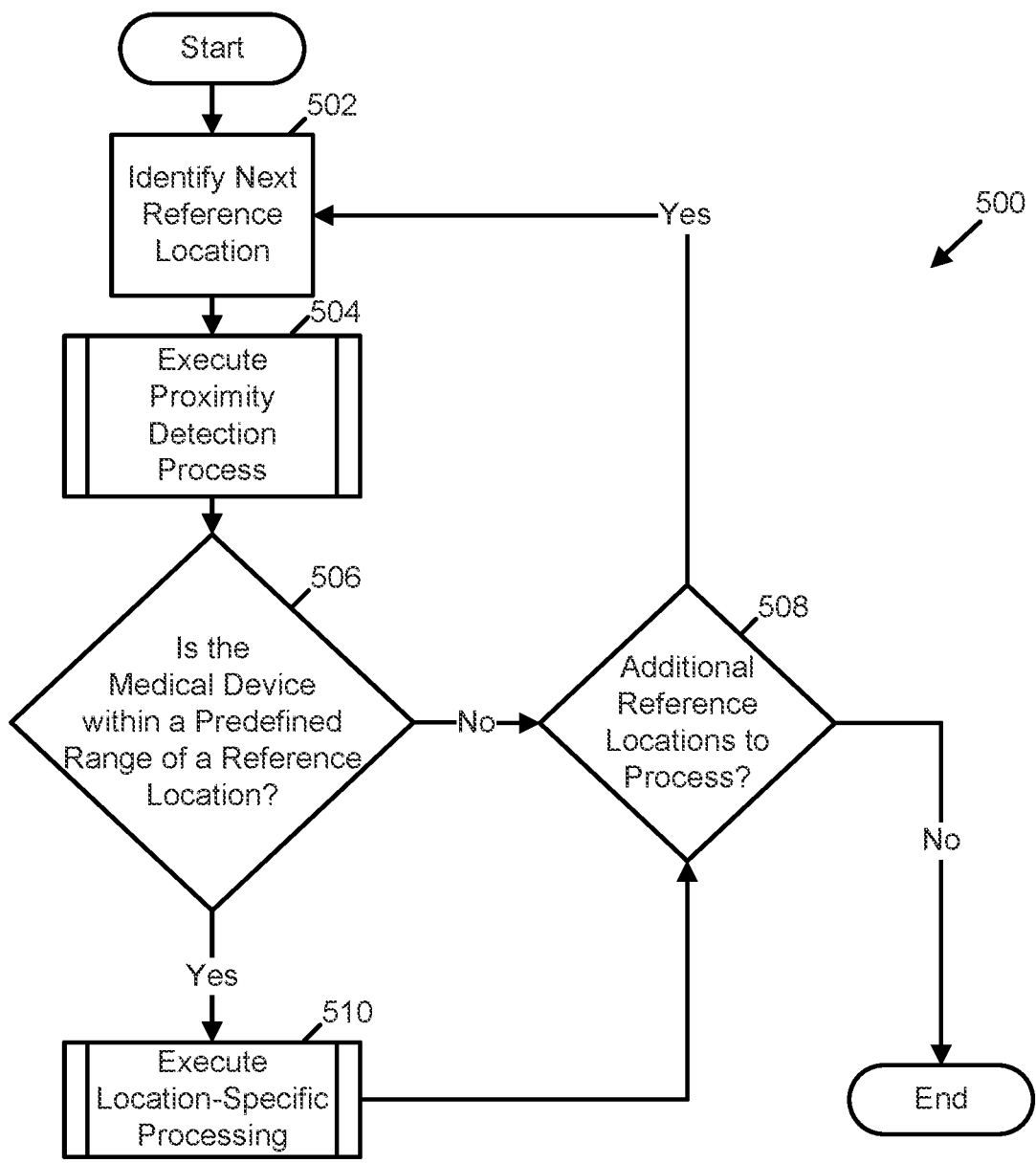
FIG. 5 is a flow diagram illustrating one example of a proximity monitoring process in accordance with an example of the present disclosure.

As described above, some examples execute one or more location aware processes. FIG. 5 illustrates one of these processes, a proximity monitoring process 500. As shown, the proximity monitoring process 500 is executed by a proximity monitoring component (e.g., the proximity monitoring component 414) of a controller (e.g., the controller 120) of a medical device (e.g., the medical device 100).

At a high level, proximity monitoring process 500 involves stepping through a predetermined plurality of reference locations stored in a data structure in, for example, location data store 430. In some examples, the plurality of reference locations may be stored at a remote location (e.g., a server accessible via the network interface 406) and made available to the proximity monitoring process 500. For example, the plurality of reference locations may be pre-programmed into the controller 120 or a remote server database. In some implementations, the controller 120 may be configured to allow a patient or other non-patient user (e.g., a patient service representative) to add one or more new reference locations to the location data store 430 for processing in accordance with the examples below.

For each reference location of the plurality of reference locations, the process 500 checks to see if the location of the controller 120 is within range of the reference location. For example, the process 500 may make use of a distance calculation of the current location of the controller 120 from the reference location (see FIG. 6) to determine whether the controller 120 is in range of a reference location. In addition or alternatively, the process 500 may detect one or more wireless network identifiers, for example, in order to determine whether the controller 120 is in range of a reference location.

The proximity monitoring process 500 starts in act 502, where the proximity monitoring component identifies data descriptive of a reference location of a plurality of reference locations stored in the location data store 430 (e.g., in a first pass of process 500, the process 500 may begin with the first reference location in a list of reference locations stored in the store 430). In one implementation, the monitoring process 500 may automatically detect a reference location that the controller 120 has not previously encountered and initiate a process whereby the controller 120 can prompt the patient or other non-patient user to store the reference location and associate it with a proximity detection process for future use. The controller 120 may determine a previously unencountered location based on analyzing a patient's movements and location history over a period of time. For instance, if the controller 120 detects that a patient is often at a particular location (e.g., a relative's home) that is not in the location data store 430, the controller 120 may prompt the patient or other non-patient user to store the reference location.

As noted, the data descriptive of the plurality of reference locations may reside in one or more records in a data structure stored in a location data store (e.g., the location data store 430). In some examples, each record of this data structure includes a field storing a unique identifier of a reference location. In some of these examples, the data structure includes a plurality of such records, each record being associated with a distinct reference location. In the data structure, the unique identifier for the reference location may be associated with a user-configurable name for the reference location (e.g., a street address, name of the location, etc.) and GPS coordinates for the location.

In act 504, the proximity monitoring component executes a proximity detection process associated with a reference location of the plurality of reference locations in the data store 430. In some examples, each of the records of the data structure described in act 502 includes an identifier of a proximity detection process to be executed when attempting to determine whether the controller is within a predefined range of the reference location associated with the record. In these examples, within the act 504, the proximity monitoring component accesses this identifier within the record associated with the current reference location and executes a proximity detection process identified thereby.

In some implementations, a plurality of reference locations may be associated with a proximity detection process. For instance, a single proximity detection process may execute by periodically or aperiodically stepping through each reference location in the plurality of reference locations and checking to see if the reference location is in range of the current location of the controller 120. For example, the time period or the times at which the process is executed may be controlled through a user interface panel on the controller 120.

As described above, the proximity monitoring component may execute any of a variety of proximity detection processes to determine whether the controller is within a predefined range of (e.g., is proximal to) a reference location. In some examples, an identifier of a proximity detection process to be executed for the reference location may be stored in a field of the record of the data structure associated with the reference location. In these examples, the proximity monitoring component may identify the proximity detection process to be executed by accessing this field.

Figure 6:
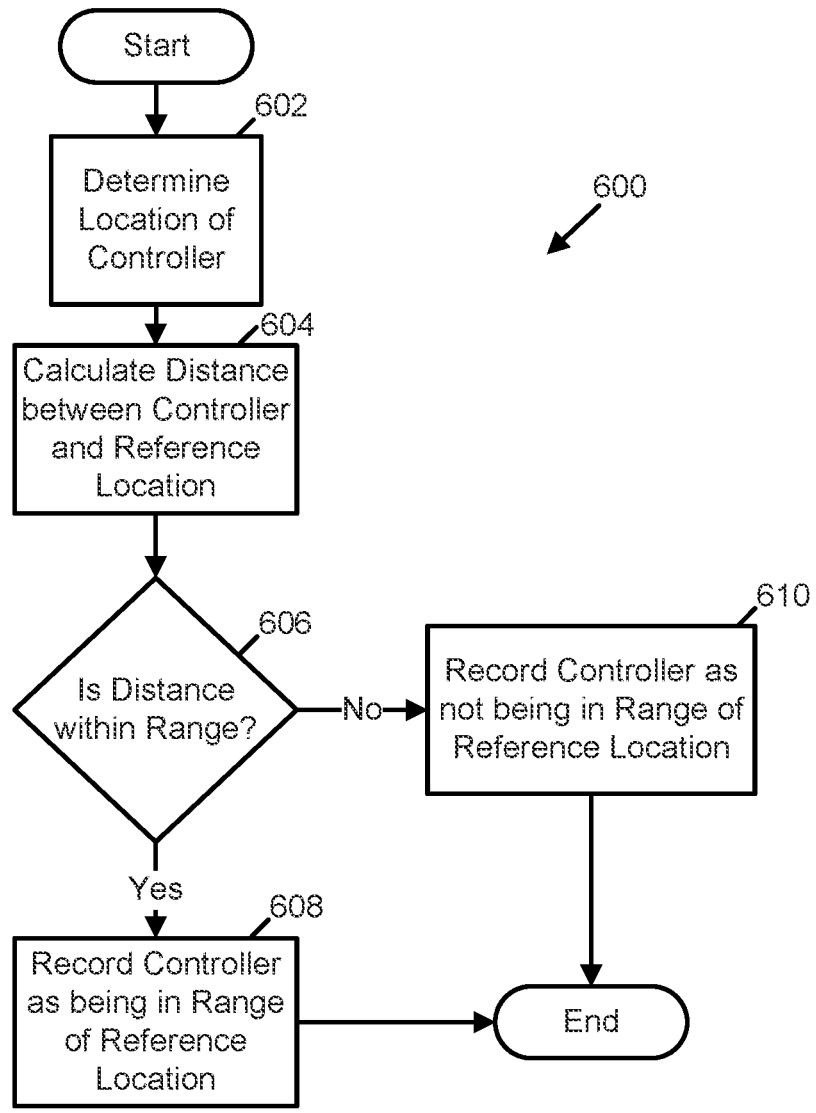
FIG. 6 is a flow diagram illustrating one example of a proximity detection process in accordance with an example of the present disclosure.

FIG. 6 illustrates one example of a proximity detection process 600 that may be executed by the proximity monitoring component in the act 504. As shown in FIG. 6, the proximity detection process 600 begins with act 602 where the proximity monitoring component determines the location of the controller within a coordinate system, such as a geographic coordinate system.

In the act 602, the proximity monitoring component determines the location of the controller within the coordinate system using any of a variety of technologies and techniques. For instance, according to one example, the proximity monitoring component includes a GPS receiver that provides a fix for the location of the controller. In another example, the proximity monitoring component includes an accelerometer and combines a previously recorded location (e.g. a GPS fix) with movement information generated from the accelerometer to determine the location. In another example, the proximity monitoring component interoperates with a network interface (e.g., the network interface 406) to calculate one or more strengths of one or more signals received from one or more network sources (e.g., cellular towers, network access points, BLUETOOTH transmitters, BLE beacons, WiFi access points, RFID tags, other medical devices, etc.) that are associated with one or more recorded locations and determines the location of the controller based on the one or more recorded locations and the one or more calculated signal strengths. In another example, the proximity monitoring component interoperates with a microphone included in the user interface 408 to scan for one or more audio signals that are associated with one or more recorded locations and determines the location of the controller based on the one or more recorded locations and the amplitude of the one or more audio signals. In another example, the proximity monitoring component interoperates with a 2D and/or 3D camera included in the user interface 408 to scan for one or more visual fiduciaries that are associated with one or more recorded locations and determines the location of the controller based on the one or more recorded locations and a distance to the visual fiduciaries. The proximity monitoring component may determine the location of the controller within the coordinate system other of technologies and techniques and the examples disclosed herein are not limited to a particular technology or technique.

In act 604, the proximity monitoring component calculates a distance between the current reference location and the location of the controller. In act 606, the proximity monitoring component determines whether the calculated distance is within a predefined range of distance values. If so, the proximity monitoring component executes act 608. If the proximity monitoring component determines that the calculated distance is not within the predefined range, the proximity monitoring component executes act 610.

In the act 608, the proximity monitoring component stores an indication that the controller is within the predefined range of the current reference location. In the act 610, the proximity monitoring component stores an indication that the controller is not within the predefined range of the current reference location. After executing either the act 608 or the act 610, the proximity monitoring component terminates the proximity detection process 600 and returns to the proximity monitoring process 500.

Processes in accord with the proximity detection process 600 enable a medical device to determine whether the medical device is within a predefined range (e.g., 100 feet) to a reference location, thereby enabling the medical device to execute (or not execute) subsequent processes that are relevant to the reference location and predefined range.

Figure 7:
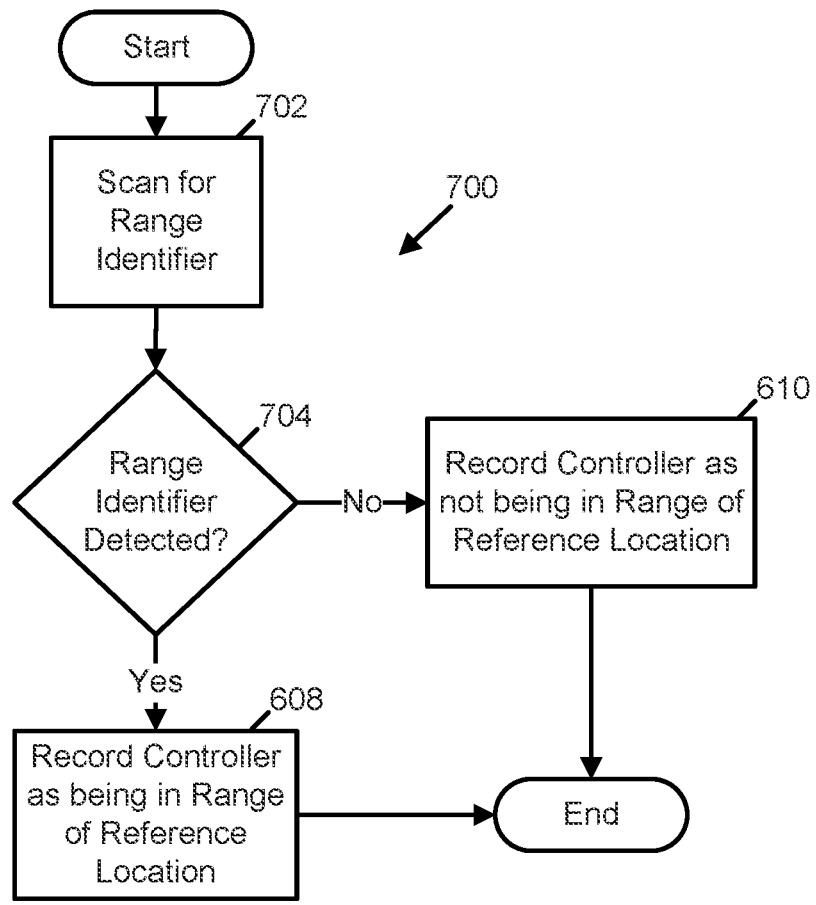
FIG. 7 is a flow diagram illustrating another example of a proximity detection process in accordance with an example of the present disclosure.

FIG. 7 illustrates another example of a proximity detection process 700 that may be executed by the proximity monitoring component in the act 504. As shown in FIG. 7, the proximity detection process 700 begins with act 702 where the proximity monitoring component scans for one or more range identifiers associated with a reference location of a plurality of reference locations. These one or more range identifiers may take a variety of forms and may be stored in one or more fields of the record of the data structure associated with the reference location. In some examples, the proximity monitoring component may identify the one or more range identifiers by accessing the one or more fields. In one example, the proximity monitoring component interoperates with the network interface 406 to scan for one or more network identifiers (e.g. service set identifiers (SSIDs), etc.) identified as one or more range identifiers for the reference location. In another example, the proximity monitoring component interoperates with the network interface 406 to scan for one or more network device identifiers (e.g. transport control protocol/internet protocol addresses, etc.) identified as one or more range identifiers for the reference location. In another example, the proximity monitoring component includes an RFID reader and scans for one or more RFID tags identified as one or more range identifiers for the reference location. In another example, the proximity monitoring component interfaces with a 2D/3D camera included in the user interface 408 to scan for one or more visual fiduciaries identified as one or more range identifiers for the reference location. In another example, the proximity monitoring component interfaces with a microphone included in the user interface 408 to scan for one or more audio signals identified as one or more range identifiers for the reference location. In another example, the proximity monitoring component includes an accelerometer and scans for one or more motion patterns identified as one or more range identifiers for the reference location. This motion pattern may be generated by (and thus follow) a commute or trip via car, bus, train, airplane, or boat. The proximity monitoring component may scan for other range identifiers and the examples disclosed herein are not limited to a particular range identifier or set of range identifiers.

In act 704, the proximity monitoring component determines whether any range identifier scanned for in the act 702 was detected. If so, the proximity monitoring component executes act 608. If the proximity monitoring component determines that no range identifier scanned for in the act 702 was detected, the proximity monitoring component executes act 610.

After executing either the act 608 or the act 610, the proximity monitoring component terminates the proximity detection process 700 and returns to the proximity monitoring process 500.

Processes in accord with the proximity detection processes 600 and 700 enable a medical device to determine whether the medical device is within a predefined range (e.g., 100 feet) of a reference location, thereby enabling the medical device to execute (or not execute) subsequent processes that are relevant to the reference location and predefined range.

Returning to FIG. 5, in act 506, the proximity monitoring component determines whether the medical device is within a predefined range of a reference location of a plurality of reference locations. In at least one example, the proximity monitoring component makes this determination by accessing an indicator stored by the proximity monitoring component during execution of either the act 608 or the act 610. Where the proximity monitoring component determines that the medical device is within the predefined range of a reference location, the proximity monitoring component executes act 510. Where the proximity monitoring component determines that the medical device is not within the predefined range of a reference location, the proximity monitoring component executes act 508.

In the act 510, the proximity monitoring component executes one or more location-specific processes that are associated with the predefined range identified in the act 506. In some examples, one or more identifiers of the one or more location-specific processes executed for the current reference location and/or predefined range are stored in one or more fields of the record of the data structure associated with each of the plurality of reference locations. In these examples, the proximity monitoring component may identify the one or more location-specific processes to be executed by accessing the one or more fields.

In some examples of the act 510, the proximity monitoring component interoperates with a location adaption component (e.g., the location adaptation component 410) and/or a location-specific processing component (e.g., the location-specific processing component 416) to execute the one or more location-specific processes. As such, the location-specific processing executed may include tasks that issue localized notifications to the patient and/or other recipients and/or other tasks. The location-specific processing may also adapt the user interface of the medical device to increase its relevance to persons associated with the predefined range.

For instance, in some examples of the act 510, the proximity monitoring component initiates execution of the location-specific processing component. In these examples, the location-specific processing component executes tasks that generate and issue one or more notifications associated with a particular reference location of a plurality of reference locations. These notifications may include, among other such notifications, reminders to service the medical device (e.g., change a battery, replace an electrode, etc.) when the patient is within range of a battery charger or area having additional/alternative electrodes, or reminders for the patient to take medication, instructions for the patient to perform a test (e.g., a six minute walk test), reminders to download or install an available software update, reminders to download or apply available changes to one or more operating parameters (e.g., monitoring, treatment or other patient parameters), reminders to download or apply available changes to one or more device configuration parameters, and/or instructions for the patient to complete a training program (e.g., when the patient is at home). In certain implementations, the device may first determine that the next opportunity for such task(s) may not be for a period of time (e.g., the patient is about to leave home for work) and issue the reminders while the patient is still at home. For example, the device may base its decision-making process on one or more template schedules as described in further detail below. Alternatively or in addition, the device may take into account a criticality indication associated with the one or more reminders (e.g., an indication that the proposed task(s) is important or critical and needs to be performed as soon as possible) in determining whether to issue the reminder while the device is within range of a reference location. In some instances, a next reference location that the patient is expected to be within range may not be equipped with the necessary features for performing certain task(s). As described below, the device may take this into account in determining whether and when to issue notifications to perform the task(s). The location-specific processing component may issue these notifications to a variety of recipients including, for example, programmable devices associated with the patient, bystanders, caregivers near the patient, and caregivers remote from the patient. As such, the location-specific processing component may issue notifications using a variety of channels including the user interface and the network interface.

In another example of act 510, location-specific processing may include one or more automatically initiated tasks performed by the device upon detecting proximity to a reference location. For example, such tasks may include automatic download/upload or updates of data or software on determining proximity to a base station or other reference location. In certain implementations, the device may first determine that the next opportunity for such task(s) may not be for a period of time (e.g., the patient is about to leave home for work) and enable the task(s) while the patient is still at home. For example, the device may base its decision making process on one or more template schedules as described in further detail below. Alternatively or in addition, the device take into account a criticality indication associated with the one or more task(s) (e.g., an indication that the proposed task(s) is important or critical and needs to be performed as soon as possible) in determining whether to perform the task which the device is within range of a reference location. In some instances, a next reference location that the patient is expected to be within range may not be equipped with the necessary features for performing certain task(s). As described below, the device may take this into account in determining whether and when to perform the task(s). Other automated tasks may include automatically initiating instructions for the patient to perform a test (e.g., a six minute walk test), downloading or installing available software updates (e.g., upgrades or patches), downloading or applying available changes to one or more operating parameters (e.g., monitoring, treatment or other patient parameters), downloading or applying available changes to one or more device configuration parameters, and/or automatically initiating a training program for the patient to complete, e.g., when the patient is at home.

Figure 8:
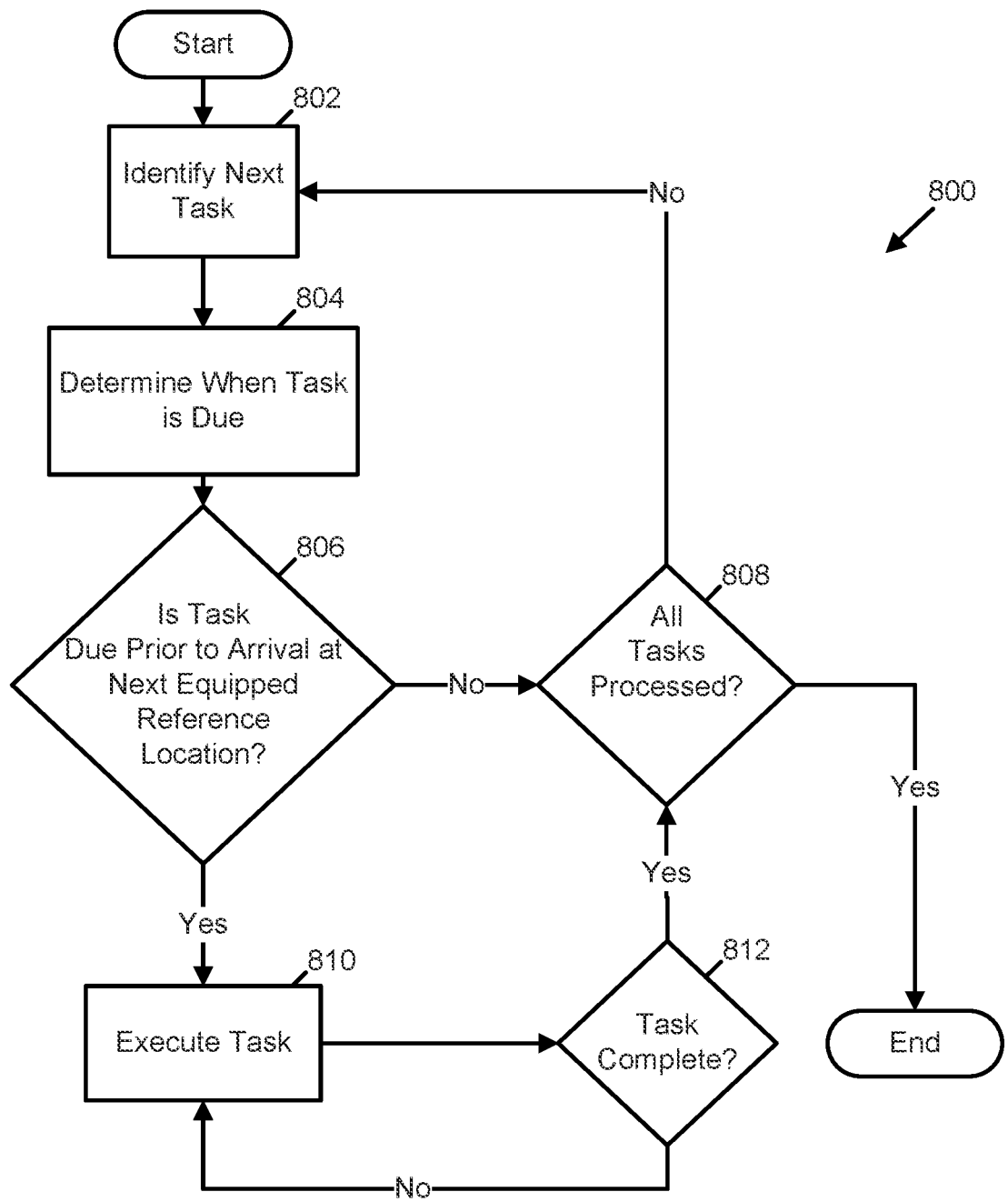
FIG. 8 is a flow diagram illustrating one example of a location-specific process in accordance with an example of the present disclosure.

FIG. 8 illustrates a location-specific process 800 executed by the location-specific processing component in accordance with some examples. Once the controller 120 has determined that the patient is within range of a particular reference location, the controller 120 may then assess whether there are any manual or automated tasks that need to be completed prior to the next time the patient returns to the same reference location or is at a different reference location that is equipped to allow for the manual or automated task to be performed at that location. For example, a manual task may be charging a battery pack of the device. If the controller 120 determines that the battery will need to be charged prior to the patient returning to within range of a battery charger, then the location-specific processing component may prompt the patient to charge the battery before leaving the reference location. As described above, automated tasks may include providing notifications or reminders with respect to manual tasks, or automatically initiating automated tasks, such as, providing instructions for the patient to perform a test (e.g., a six minute walk test), downloading or installing available software updates, upgrades, or patches, downloading or applying available changes to one or more operating parameters (e.g., monitoring, treatment or other patient parameters), downloading or applying available changes to one or more device configuration parameters, and/or automatically initiating a training program for the patient to complete, e.g., when the patient is at home.

In this regard, as shown, the location-specific process 800 begins with act 802 where the location-specific processing component identifies a task of a plurality of tasks associated with a reference location of a plurality of reference locations. Examples of tasks that may be identified include tasks to service the medical device (e.g., change or charge a battery, replace an electrode, etc.), to take medication, to perform a diagnostic test (e.g., a six minute walk test) or remedial physical activity, to complete a training program, etc. For instance, in one example, the task is to service a serviceable component of the medical device. This serviceable component may be, for example, a battery (e.g. the battery 212), a garment (e.g., the garment 110), or any other component of the medical device.

In act 804, the location-specific processing component identifies a time when the task is scheduled for completion. For example, where the task is to service a serviceable component, the location-specific processing component determines when service is next due for the serviceable component. In some examples, the location-specific processing component makes this determination by accessing a service schedule for the serviceable component. This service schedule may be stored in the location data store and may include information descriptive of one or more historical dates and times when the serviceable component was serviced. For example, where the unprocessed serviceable component is the garment, the service schedule may include a date and time that the garment was last laundered. Where the unprocessed serviceable component is the battery, the service schedule may include a date and time that the battery was last replaced. The service schedule may also include information descriptive of the next date and time that the serviceable component is due for service. For example, where the serviceable component is the garment, the service schedule may include a date and time that the garment is due to be laundered. Where the serviceable component is the battery, the service schedule may include a date and time that the battery's remaining runtime will expire and/or a date and time when the battery's remaining service life will expire.

In some examples, the location-specific processing component determines when service is next due by assessing the current state of the serviceable component. For example, where the serviceable component is the battery, the location-specific processing component may run a diagnostic of the battery to estimate a date and time that the battery's remaining runtime will expire and/or a date and time when the battery's remaining service life will expire.

In act 806, the location-specific processing component determines whether the task is due prior to the controller's arrival at a next reference location associated with facilities capable of completing the task. Where the task is to service a serviceable component, the location-specific processing component determines whether service is due for the serviceable component prior to the controller's arrival at a next service location (e.g., a reference location associated with equipment useful in servicing the serviceable component). In some examples, the location-specific processing component makes this determination by accessing a template schedule stored in the location data store. The template schedule may include a chronology of reference locations routinely visited by the patient. In some examples, the chronology specifies both arrival and departure dates and times for each visitation of reference location. The template schedule may be configured during an initial fitting of the medical device to the patient and periodically adjusted by artificial intelligence processes (e.g., the machine learning process described below with reference to FIG. 9).

In some examples of the act 806, the location-specific processing component determines whether service is due by projecting the date and time when service is next due for the serviceable component (as determined in the act 804) onto the template schedule and identifying any service locations beyond the current service location that are scheduled to be visited prior to the date and time when service is due. For example, where the serviceable component is the garment, the location-specific processing component may identify service locations (e.g., that are associated with laundering facilities) that the controller is projected to visit before laundering is next due. Where the unprocessed service component is the battery, the location-specific processing component may identify service locations (e.g., that are associated with battery chargers and replacement batteries) that the controller is projected to visit before battery charging and/or replacement is next due. If the location-specific processing component does not to identify at least one service location scheduled to be visited prior to the date and time service is due, the location-specific processing component executes act 810. If the location-specific processing component identifies one or more service locations to be visited prior to the date and time service is due, the location-specific processing component executes act 808.

In the act 810, the location-specific processing component executes the task by issuing a notification to a recipient requesting that the task be completed prior to departure from the current reference location and/or automatically executing the task. For example, where the task is to service a serviceable component, the location-specific processing component issues a notification to a recipient requesting that the serviceable component be serviced prior to departure from the current service location. The recipient of this notification may be a programmable device (e.g., the medical device or a smart phone) associated with the patient, a programmable device associated with a caregiver with the patient, or a programmable device associated a caregiver not with the patient. Where the task is to update configuration information of the medical device, the location-specific processing component updates the configuration information by downloading and applying updated configuration information.

In act 812, the location-specific processing component determines whether the task has been completed. In some examples, the location-specific processing component makes this determination in response to a reply to the notification issued in the act 810. This reply may be submitted by the recipient. For example, where the task is to service a serviceable component, the location-specific processing component determines whether the serviceable component has been serviced. In at least one example, the location-specific processing component makes this determination (or verifies a determination based on the reply) by assessing the status of the serviceable component. For example, where the serviceable component is the garment, the location-specific processing component determines the garment has been laundered by analyzing input indicating the same received via the user interface. Where the serviceable component is the battery, the location-specific processing component determines the battery has been recharged and/or replaced by running a diagnostic on the battery. If the location-specific processing component does not verify, within a configurable timeout period, that the serviceable component was serviced, the location-specific processing component executes act 810. If the location-specific processing component verifies, within the configurable timeout period, that the serviceable component was serviced, the location-specific processing component updates the historical dates and times and/or the next date and time stored in the service schedule for the serviceable component and executes act 808.

In the act 808, the location-specific processing component determines whether additional tasks associated with the reference location and/or a predefined range of the reference location exist. If so, the location-specific processing component executes the act 802. If no additional unprocessed tasks exist, the location-specific processing component terminates the location-specific process 800.

Processes in accord with the location-specific process 800 enable a medical device to remind users (e.g., patient, caregivers, etc.) of tasks to complete when the users are in a convenient location to do so.

Figure 9:
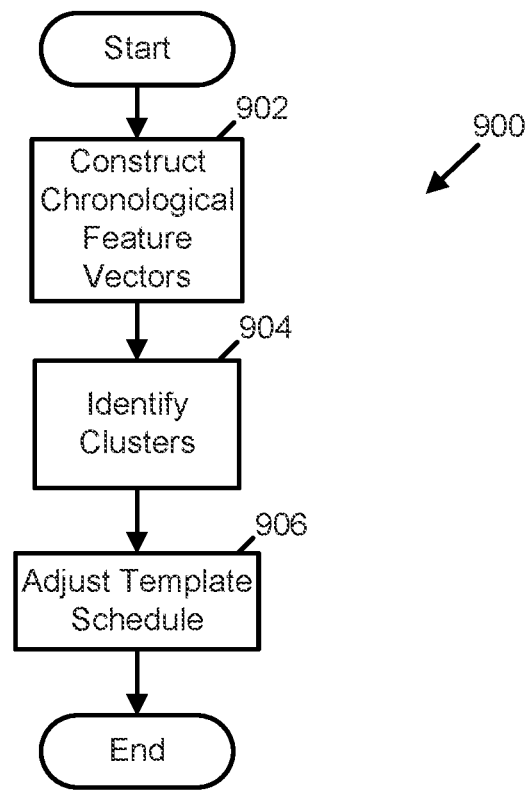
FIG. 9 is a flow diagram illustrating one example of a template schedule adaptation process in accordance with an example of the present disclosure.

As described above with reference to the act 806, some examples implement machine learning processes that adjust the template schedule based on the recorded movement of the controller and/or the patient. FIG. 9 illustrates a machine learning process 900 in accordance with these examples. As shown, the machine learning process 900 starts with act 902 where the location-specific processing component constructs feature vectors descriptive of sampled movement observations of the controller. These feature vectors may include elements descriptive of a location visited, a duration of the visitation, a start time of the visitation, an end time of the visitation, the day of the week of the visitation, etc.

In act 904, the location-specific processing component identifies clusters of feature vectors. Within the act 904, the location-specific processing component may execute any of a variety of clustering processes (e.g., k-means process) to identify clusters and centroids within the feature vectors generated in the act 902.

In act 906, the location-specific processing component calculates a distance (e.g., a cosine distance) between each of the centroids identified in the act 904 and visitation feature vectors descriptive of each visitation scheduled in the chronology of template schedule. Next, the location-specific processing component associates a centroid with each visitation feature vector (e.g., the centroid closest to the visitation feature vector). In this way, the location-specific processing component identifies centroids that are closest to the existing template schedule. Next, within the act 906, the location-specific processing component compares the distance between each centroid and its associated visitation feature vector and, where the distance transgresses a threshold, adjusts the visitation schedule in the chronology such that the visitation feature vector is brought within the threshold distance of its associated centroid. After executing the act 906, the location-specific processing component terminates the machine learning process 900.

Processes in accord with the machine learning process 900 enable a medical device to adaptively adjust a template schedule based on empirical data, thereby increasing the likelihood of the schedule being followed and the relevance of notifications based on thereon.

Figure 10:
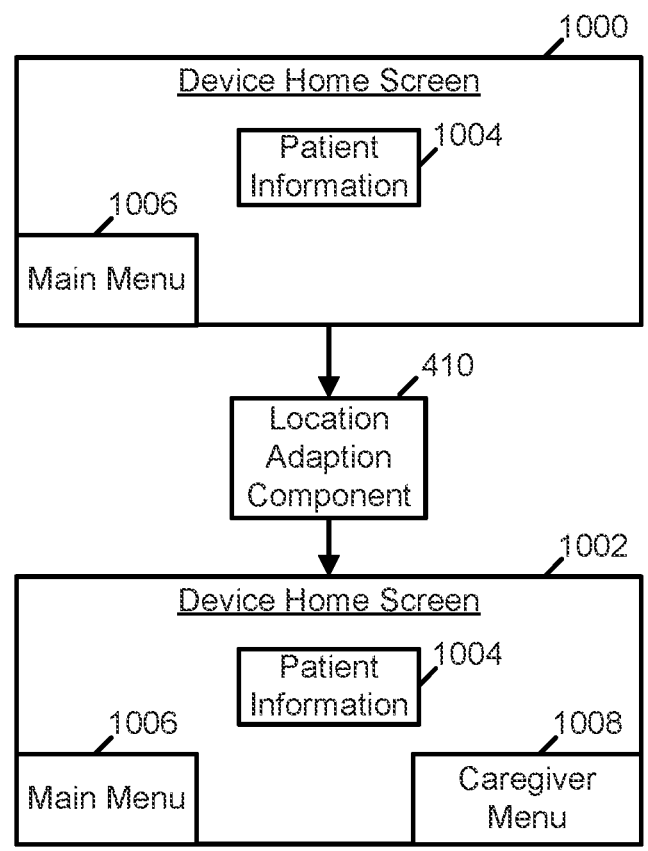
FIG. 10 is a block diagram of screens illustrating an adaptation by one or more location aware components in accordance with examples of the present disclosure.

In another example of the act 510, the proximity monitoring component initiates execution of the location adaptation component. The location adaptation component, in turn, adapts the operation of the medical device. For instance, in one example, the location adaptation component alters the information and/or options displayed via the user interface. FIG. 10 illustrates the effect of an adaptation process executed by the location adaptation component.

As shown, FIG. 10 illustrates the location adaptation component 410, device home screen 1000, and device home screen 1002. The device home screen 1000 includes patient information 1004, which is descriptive of the patient being treated by the medical device, and a main menu button 1006. The device home screen 1002 includes the patient information 1004, the main menu button 1006, and a caregiver menu button 1008.

In some examples, the adaptation process executed by the location adaptation component 410 identifies one or more adaptations associated with the predefined range of the current reference location and adapt the user interface in accordance with the one or more identified adaptations. For example, with reference to FIG. 10, the adaptation process identifies the caregiver menu button 1008 as being associated with the predefined range of the current reference location in the location data store and adds the caregiver menu button to the device home screen 1000 to render the device home screen 1002. In response to a selection of the caregiver menu button, the controller may provide, for example, access to historical patient information, additional configuration options, and the like.

Processes in accord with the adaptation process illustrated in FIG. 10 enable a medical device to adapt operation of a user interface for one or more predefined ranges of one or more reference locations, thereby increasing the relevance of information presented by the user interface to persons located within the one or more predefined ranges.

Returning to FIG. 5, in the act 508, the proximity monitoring component records the reference location as having been processed and determines whether additional reference locations of a plurality of reference locations exist for processing. If so, the proximity monitoring component executes the act 502. If no additional reference locations exist, the proximity monitoring component terminates the proximity monitoring process 500.

Processes in accord with the proximity monitoring process 500 enable a medical device to monitor for changes of location and execute beneficial location-specific processing based on these location changes. The proximity monitoring process 500 may be executed periodically, aperiodically, or in response to events (e.g., startup of the controller, change in available WiFi network, etc.).

Figure 11:
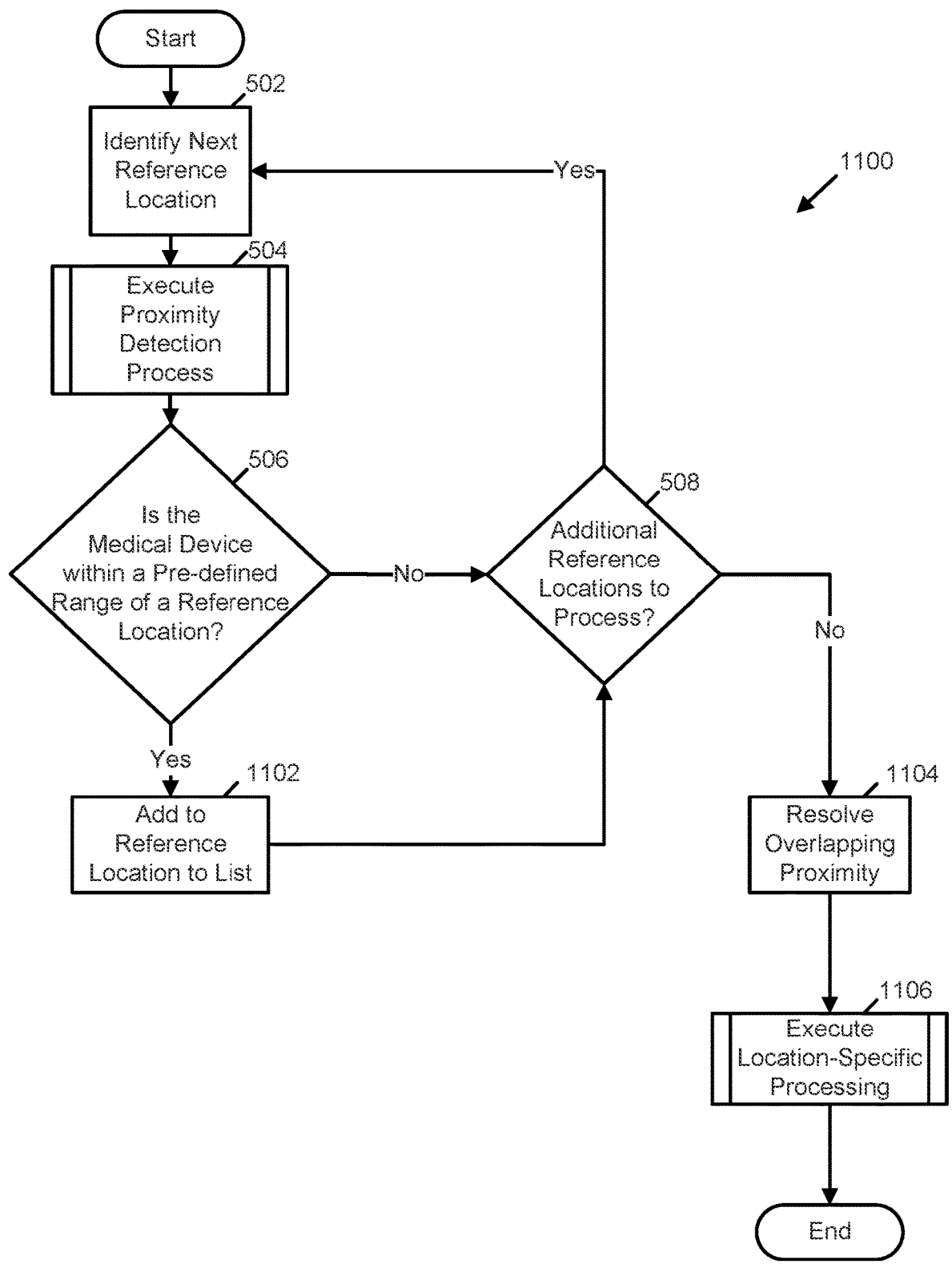
FIG. 11 is a flow diagram illustrating another example of a proximity monitoring process in accordance with an example of the present disclosure.

FIG. 11 illustrates another proximity monitoring process 1100. The proximity monitoring process 1100 may be executed by the proximity monitoring component. At a high level, the proximity monitoring process 1100 mimics the operation of the proximity monitoring process 500 and includes the acts 502, 504, 506, and 508. However, the proximity monitoring process 1100 is enhanced to provide conflict resolution between reference locations where the controller is within two or more predefined ranges of two or more reference locations.

In act 1102, the proximity monitoring component maintains a list of reference locations that are currently proximal to the medical device by adding the reference location identified in the act 506 to a list of reference locations maintained in the location data store. In act 1104, the proximity monitoring component determines whether two or more reference locations are stored in this list. If so, the proximity monitoring component executes a conflict resolution process to determine the location-specific processing to execute in act 1106. The particular conflict resolution process executed varies between examples and may include first come, first served, priority, mediation, etc. The first come, first served process resolves conflicts in favor of the reference location first detected by proximity monitoring component. The priority process requires that each reference location be associated with a priority and resolves conflicts in favor of the reference location associated with the highest priority. The mediation process resolves conflicts by allowing processing for some or all reference locations in the list. Other conflict resolution processes may be executed in the act 1104 and the examples disclosed herein are not limited to a particular conflict resolution process.

In the act 1106, the proximity monitoring component executes location-specific processing associated with one or more applicable predefined ranges of one or more reference locations favored by the conflict resolution process. In examples where a single reference location is favored over others, the act 1106 executes the tasks of the act 510. In examples where a two or more reference locations are favored, the act 1106 may execute location-specific processing associated with the two or more reference locations. For example, the location-specific processing component may issue notifications associated with two or more predefined ranges of two or more reference locations and/or the location adaptation component may execute adaptations associated with the two or more predefined ranges of the two or more reference locations.

Example Location Aware Processing System

Figure 12:
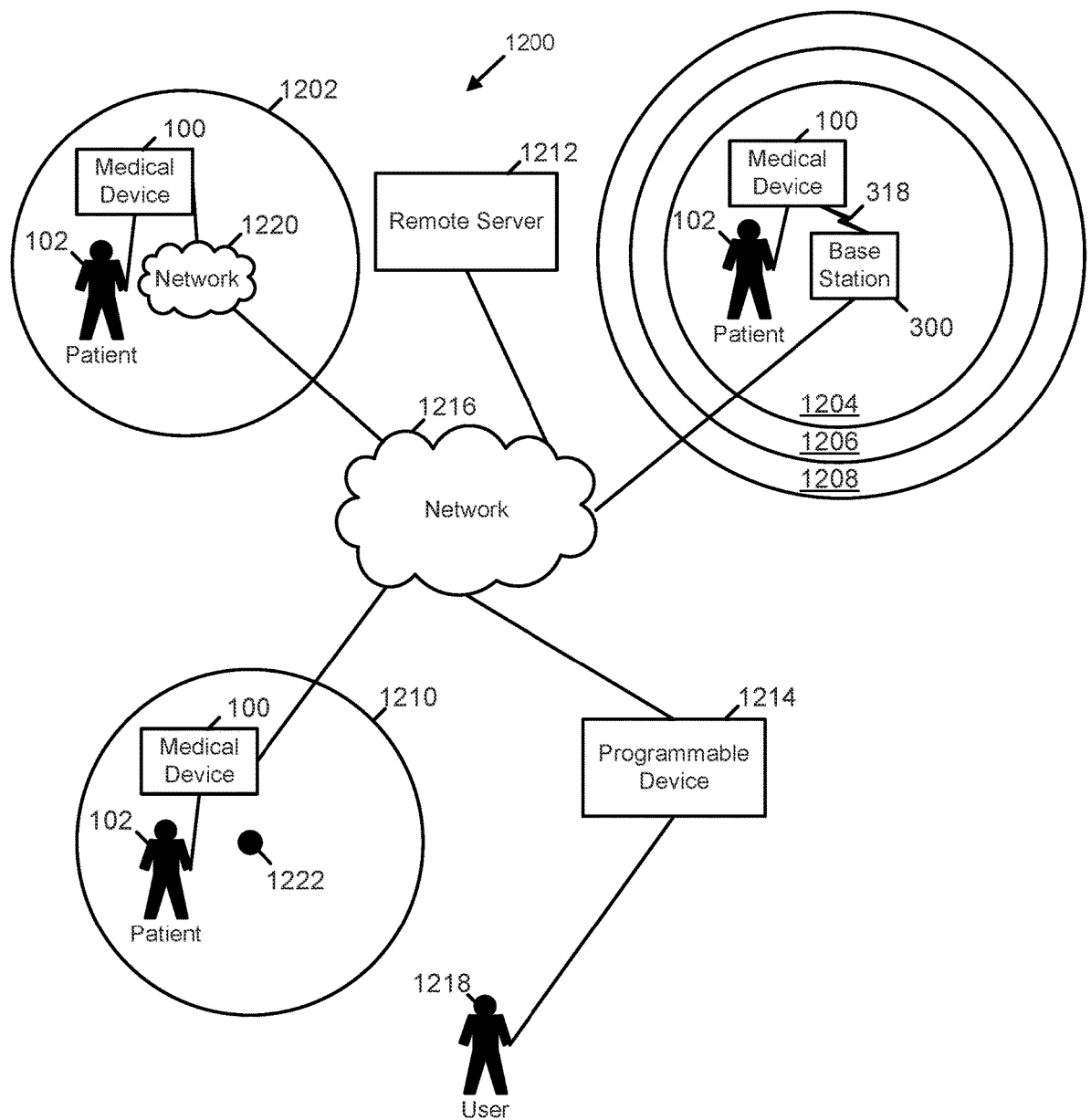
FIG. 12 is a diagram of a location aware processing system in accordance with examples of the present disclosure.

In some examples, a medical device including location aware components (e.g., the proximity monitoring component 414, the location-specific processing component 416, and the location adaptation component 410) is incorporated into a location aware processing system. FIG. 12 illustrates a location aware processing system 1200 in accordance with these examples. As shown, the location aware processing system 1200 includes the medical device 100, the base station 300, predefined ranges 1202, 1204, 1206, 1208, and 1210, a remote server 1212, a programmable device 1214, a communication network 1216, and a local communication network 1220. In this example, the medical device 100 is associated with the patient 102 and the programmable device 1214 is associated with the user 1218 (e.g., a support technician, a caregiver, etc.). The programmable device 1214 may be, for example, a computer or a handheld device such as a tablet, smartphone, or mobile device, with access to the network 1216 and associated with the user 1218. Also, as shown, the predefined range 1202 is associated with a reference location of the network 1220, the predefined ranges 1204, 1206, and 1208 are associated with a reference location of the base station 300, and the predefined range 1210 is associated with a reference location of a geographic point 1222.

As shown in FIG. 12, the medical device 100 exchanges (e.g., transmits or receives) information with the programmable device 1214 and the remote server 1212 via the network 1216. This information may include localized notifications such as those described herein to enable the user 1218 or another user with access to the remote server 1212 to monitor the status and activities of the patient 102. The network 1216 may include any communication network through which programmable devices may exchange information. In some examples, the network 1216 supports wireless network and/or wired connections. For instance, the network 1216 may support any of various networking standards such as GSM, CMDA, USB, BLUETOOTH, CAN, ZigBee, Wireless Ethernet, and TCP/IP, among other networking standards.

In various examples, the programmable device 1214 is implemented using any of a variety of programmable devices (e.g., a device with data storage and at least one processor in data communication with the data storage). In some examples, the programmable device 1214 includes a plurality of interfaces, one or more processors, and a data storage device coupled to one another via a communication mechanism, such as a bus. In these examples, the programmable device 1214 also includes a battery to power the device and may include one or more antennas. The plurality of interfaces in the programmable device 1214 include a user interface and a network interface configured to communicate with the network 1216.

FIG. 12 also illustrates the patient 102, as the patient 102 goes about her daily routine. In one example, the patient 102 begins her day at home. Her home includes the base station 300, which is in wireless communication with the medical device 100 via the network connection 318. In this example, the network connection 318 supports the IBEACON standard and the predefined ranges 1204, 1206, and 1208 respectively correspond to IBEACON range identifiers of immediate (e.g., where the medical device 100 is within centimeters of the base station 300), near (e.g., where the medical device 100 is approximately between 10 centimeters and 10 meters away from the base station 300), and far (e.g., where the medical device 100 is approximately between 10 meters and 100 meters away from the base station 300). As such, the proximity monitoring component 414 of the medical device 100 discriminates between each of the predefined ranges 1204, 1206, 1208 using these range identifiers and determines within which predefined range the medical device 100 resides as the patient 102 moves about her home.

In this example, the proximity monitoring component 414 also interoperates with the location-specific processing component 416 to issue various notifications to the patient 102 that are relevant to the patient's current location with her home. For instance, where the proximity monitoring component 414 detects that the medical device has entered either of the predefined ranges 1204 or 1206, the proximity monitoring component 414 may notify the location-specific processing component 416. The location-specific processing component 416, in turn, may check the status of the battery 212 and issue a notification to the patient 102 to change the battery 212 if the runtime of the battery 212 is below a threshold value and if the charging bay 304 of the base station 300 currently holds a charged replacement battery. Further, where the proximity monitoring component 414 detects that the medical device has moved from the predefined range 1204 to the predefined range 1208 (indicating the patient 102 may be leaving her home), the proximity monitoring component 414 notifies the location-specific processing component 416. The location-specific processing component 416, in turn, executes the location-specific process 800, determines that the garment 110 will be in need of service prior to her return home (according to the template schedule), and issues a notification to the patient to launder the garment 110 prior to leaving her home.

Continuing the example illustrated in FIG. 12, the patient 102 next visits her office. Her office includes the local network 1220, which like the network 1216 may include any communication network through which programmable devices may exchange information. As the patient 102 enters her office, the proximity monitoring component 414 identifies the SSID of the network 1220 as a range identifier of the predefined range 1202 and, consequently, determines that the medical device 100 has entered the predefined range 1202. In response to making this determination, the proximity monitoring component 414 notifies the location-specific processing component 416. The location-specific processing component 416, in turn, issues a notification to the patient to take her medicine, which is a task associated with her office desk.

In this example, the patient 102 next visits her caregiver, whose office is located at the geographic location 1222. As the patient nears her caregiver's office, the proximity monitoring component tracks the geographic location of the controller (e.g., via GPS), calculates a distance between the medical device and the geographic location 1222, and, where the distance is less than a threshold value, determines that the medical device has entered the predefined range 1210. In response to making this determination, the proximity monitoring component 414 notifies the location adaptation component 410. The location adaptation component 410, in turn, adapts the operation of the medical device so that the user interface presents the caregiver menu button 1008 on the display 220.

Other Examples

In one implementation, Bluetooth Low Energy beacon (BLE beacon) technology may be used in the base stations described above. Using this technology, a medical device can ascertain proximity, including a degree of proximity, to one or more base stations in a certain region. For example, BLE beacons associated with the bases station may periodically cast a beacon signal containing a universally unique identifier (UUID), and information regarding the location of the base station. A medical device may detect these signals and determine its proximity from the one or more base stations based on the information in the signals. The BLE beacon may include a calibration parameter indicating a nominal signal strength at a predetermined range from the beacon. Using the parameter, a medical device can measure a signal strength of a received signal to determine how close the device is to a base station. In an implementation, the medical device may include in memory a look-up table of base stations along with their known locations. Based on the signal strength, and information contained in the signal, a medical device may provide different types of notifications and/or use different notification modes based on proximity of the medical device to a base station. For example, if the medical device has a remaining battery charge below a set threshold (e.g., 25%) then the device may be configured to notify the patient in the following manner. If the patient is approximately 15 feet away from a base station (which also has charging capability), the medical device may inform the patient through a silent visual indicator that the battery is running out and because the patient is near the base station, the patient should consider charging the battery. If the patient is closer, e.g., less than 3 feet from the base station, the medical device and/or the base station may issue an audible or verbal notification requesting that the patient charge the battery as the patient is proximal to the base station.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. A medical device configured to be worn by an ambulatory patient for monitoring and treating the ambulatory patient and executing location-specific processes, the medical device comprising:
    a plurality of sensing electrodes configured to be in contact with skin and acquire electrocardiogram (ECG) data from the ambulatory patient over an extended period of time;
    a garment configured to dispose the plurality of sensing electrodes at various positions about a torso of the ambulatory patient to continuously acquire the ECG data;
    at least one therapy electrode configured to deliver a therapeutic electrical shock to the ambulatory patient;
    a battery coupled with the at least one therapy electrode to power the therapeutic electrical shock;
    a user interface; and
    at least one processor coupled with the plurality of sensing electrodes, the at least one therapy electrode, and the user interface and configured to:
        determine whether a current location of the medical device is within a predefined range of a reference location of a home of the ambulatory patient,
        determine a location-specific process to execute based on a determination that the current location is within the predefined range, the location-specific process being configured to control the user interface to notify the ambulatory patient to perform one or more home-specific actions and remind the ambulatory patient to review a patient training module, and
        execute the location-specific process to notify the ambulatory patient to perform the one or more home-specific actions.

2. The medical device of claim 1, wherein the one or more home-specific actions include one or more of change the battery, adjust at least one sensing electrode of the plurality of sensing electrodes, or launder the garment.

3. The medical device of claim 1, further comprising a memory storing a list of reference locations, the list including the reference location of the home of the ambulatory patient.

4. The medical device of claim 3, wherein:
    the list of reference locations further comprises a reference location of a workplace of the ambulatory patient and a network identifier associated with the workplace; and
    the at least one processor is further configured to determine that the current location of the medical device is within a predefined range of the reference location of the workplace of the ambulatory patient based on detecting the network identifier.

5. The medical device of claim 3, wherein:
    the list of reference locations further comprises a reference location of a caregiver of the ambulatory patient;
    the at least one processor is further configured to, in response to determining that the current location of the medical device is within a predefined range of the reference location of the caregiver of the ambulatory patient, adapt the user interface to grant access to functionality associated with the caregiver.

6. The medical device of claim 1, wherein:
    the at least one processor is further configured to identify a next scheduled visitation to the home of the ambulatory patient; and
    the at least one processor is further configured to determine the location-specific process to execute further based on determining that a serviceable component of the medical device should be serviced before the next scheduled visitation to the home of the ambulatory patient.

7. The medical device of claim 6, wherein the at least one processor is further configured to adjust a schedule listing scheduled visitations to the home of the ambulatory patient based on sampled movement observations of the ambulatory patient.

8. The medical device of claim 1, wherein:
    the at least one processor is further configured to determine whether the current location of the medical device is within a predefined range of an alternative reference location; and
    the at least one processor is further configured to execute a conflict resolution process to determine whether to execute a location-specific process associated with the home of the ambulatory patient or an alternative location-specific process associated with the alternative reference location.

9. The medical device of claim 8, wherein the conflict resolution process resolves conflicts based on a predefined range within which the medical device is first detected.

10. The medical device of claim 8, wherein the conflict resolution process resolves conflicts based on location priorities specified in a list of reference locations that includes the reference location of the home of the ambulatory patient.

11. The medical device of claim 1, wherein the reference location of the home of the ambulatory patient is included in a list of reference locations that is stored in a remote server database.

12. The medical device of claim 1, wherein:
    the location-specific process is configured to control the user interface to notify the ambulatory patient to launder the garment; and
    the at least one processor is further configured to determine the location-specific process to execute further based on a date and/or time that the garment was last laundered.

13. The medical device of claim 1, wherein:
    the location-specific process is configured to control the user interface to notify the ambulatory patient to change the battery; and
    the at least one processor is further configured to determine the location-specific process to execute further based on a first additional determination that the battery holds a remaining charge that is less than a specified value.

14. The medical device of claim 13, wherein the at least one processor is further configured to determine the location-specific process to execute further based on a second additional determination that the home of the ambulatory patient has a base station with a charging bay that currently holds a charged replacement battery.

15. The medical device of claim 14, wherein controlling the user interface to notify the ambulatory patient to change the battery comprises:
generating a silent visual indicator via the user interface when the current location is within a first range of the base station; and
generating an audible notification when the current location is within a second range of the base station.

16. The medical device of claim 15, wherein the second range is smaller than the first range.

17. The medical device of claim 1, wherein determining whether the current location of the medical device is within the predefined range of the reference location of the home of the ambulatory patient further comprises determining that the current location of the medical device has left a first predefined range while remaining within a second predefined range, wherein the second predefined range encompasses the first predefined range.

18. The medical device of claim 1, wherein the at least one processor is configured to determine whether the current location of the medical device is within the predefined range in response to at least one of expiration of a timer or receipt of a request to determine whether the current location is within the predefined range.

19. The medical device of claim 18, further comprising a network interface coupled with the at least one processor, wherein the at least one processor is further configured to operate the network interface in a power conservation mode when not determining whether the current location of the medical device is within the predefined range.

20. The medical device of claim 18, further comprising a network interface coupled with the at least one processor, wherein the at least one processor is further configured to operate the network interface in a power conservation mode when the battery holds a remaining charge that is less than a specified value.

21. The medical device of claim 1, further comprising a network interface, the location-specific process further being configured to control the network interface to transmit a notification of a status of the medical device.

22. The medical device of claim 1, wherein the location-specific process is further configured to control the user interface to notify the ambulatory patient to take a medication.

23. A medical device configured to be worn by an ambulatory patient for monitoring and treating the ambulatory patient and executing location-specific processes, the medical device comprising:
a memory storing a list of reference locations, the list including a home reference location corresponding to a home of the ambulatory patient and a caregiver reference location corresponding to a caregiver of the ambulatory patient;
a plurality of sensing electrodes configured to be in contact with skin and acquire electrocardiogram (ECG) data from the ambulatory patient over an extended period of time;
a garment configured to dispose the plurality of sensing electrodes at various positions about a torso of the ambulatory patient to continuously acquire the ECG data;
at least one therapy electrode configured to deliver a therapeutic electrical shock to the ambulatory patient;
a battery coupled with the at least one therapy electrode to power the therapeutic electrical shock;
a user interface; and
at least one processor coupled with the plurality of sensing electrodes, the at least one therapy electrode, and the user interface and configured to:
determine whether a current location of the medical device is within a first predefined range of the home reference location,
determine whether the current location of the medical device is within a second predefined range of the caregiver reference location,
determine a location-specific process to execute based on a determination that the current location is within the first predefined range, the location-specific process being configured to control the user interface to notify the ambulatory patient to perform one or more home-specific actions,
in response to determining that the current location of the medical device is within the second predefined range, adapt the user interface to grant access to functionality associated with the caregiver, and
execute the location-specific process to notify the ambulatory patient to perform the one or more home-specific actions.

24. The medical device of claim 23, wherein the location-specific process is configured to control the user interface to notify the ambulatory patient to change the battery.

25. The medical device of claim 23, wherein the at least one processor is further configured to determine the location-specific process to execute further based on an additional determination that the battery holds a remaining charge that is less than a specified value.

26. A medical device configured to be worn by an ambulatory patient for monitoring and treating the ambulatory patient and executing location-specific processes, the medical device comprising:
a plurality of sensing electrodes configured to be in contact with skin and acquire electrocardiogram (ECG) data from the ambulatory patient over an extended period of time;
a garment configured to dispose the plurality of sensing electrodes at various positions about a torso of the ambulatory patient to continuously acquire the ECG data;
at least one therapy electrode configured to deliver a therapeutic electrical shock to the ambulatory patient;
a battery coupled with the at least one therapy electrode to power the therapeutic electrical shock;
a user interface; and
at least one processor coupled with the plurality of sensing electrodes, the at least one therapy electrode, and the user interface and configured to:
determine whether a current location of the medical device is within a predefined range of a reference location of a home of the ambulatory patient,
determine a location-specific process to execute based on a determination that the current location is within the predefined range, and further based on a date and/or time that the garment was last laundered, wherein the location-specific process is configured to control the user interface to notify the ambulatory patient to perform one or more home-specific actions and launder the garment, and
execute the location-specific process to notify the ambulatory patient to perform the one or more home-specific actions.

27. The medical device of claim 26, wherein the at least one processor is configured to determine whether the current location of the medical device is within the predefined range in response to at least one of expiration of a timer or receipt of a request to determine whether the current location is within the predefined range.

28. The medical device of claim 26, wherein the location-specific process is further configured to control the user interface to remind the ambulatory patient to take a medication.

\* \* \* \* \*